United States Patent [19]

Kurozumi et al.

[11] 4,132,726

[45] Jan. 2, 1979

[54] PROCESS FOR THE PREPARATION OF 4-HYDROXYCYCLOPENT-2-EN-1-ONE DERIVATIVES

[75] Inventors: Seizi Kurozumi; Takeshi Toru; Toshio Tanaka; Shuzi Miura; Makiko Kobayashi, all of Hino; Sachio Ishimoto, Tokyo; Sadakazu Matsubara, Hino, all of Japan

[73] Assignee: Teijin Limited, Osaka, Japan

[21] Appl. No.: 642,800

[22] Filed: Dec. 22, 1975

[30] Foreign Application Priority Data

| Dec. 27, 1974 | [JP] | Japan | 49-149013 |
|---|---|---|---|
| Dec. 27, 1974 | [JP] | Japan | 49-149014 |
| Mar. 13, 1975 | [JP] | Japan | 50-29486 |
| Apr. 17, 1975 | [JP] | Japan | 50-45791 |
| Apr. 17, 1975 | [JP] | Japan | 50-45792 |
| Apr. 17, 1975 | [JP] | Japan | 50-45793 |
| Apr. 21, 1975 | [JP] | Japan | 50-47399 |
| Apr. 21, 1975 | [JP] | Japan | 50-47400 |
| Apr. 21, 1975 | [JP] | Japan | 50-47401 |
| Apr. 21, 1975 | [JP] | Japan | 50-47402 |
| May 5, 1975 | [JP] | Japan | 50-62985 |

[51] Int. Cl.² ............................................. C07F 7/18
[52] U.S. Cl. ...................... 260/448.8 R; 260/345.9 P; 260/463; 260/586 R; 260/590 C; 568/838; 568/667; 560/262; 560/106; 560/60
[58] Field of Search .................... 260/448.8 R, 345.9, 260/488 R, 469, 473 A, 586 R

[56] References Cited

U.S. PATENT DOCUMENTS

| 2,951,057 | 8/1960 | Wiese et al. | 260/448.8 R X |
|---|---|---|---|
| 2,957,901 | 10/1960 | Olson et al. | 260/448.8 R |
| 2,974,157 | 3/1961 | Jex | 260/448.8 R |
| 3,843,704 | 10/1974 | Hetzel | 260/448.8 R |
| 3,852,097 | 12/1974 | Owen et al. | 260/448.8 R X |
| 3,856,843 | 12/1974 | Nagai et al. | 260/448.8 R |
| 3,922,436 | 11/1975 | Bell et al. | 260/448.8 R X |
| 3,954,835 | 5/1976 | Samuelson et al. | 260/448.8 R X |

Primary Examiner—Paul F. Shaver
Attorney, Agent, or Firm—Sherman & Shalloway

[57] ABSTRACT

Novel optically active compounds of 4-protected hydroxy-cyclopent-2-en-1-ones of the formula

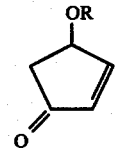

(2)

wherein R is a splittable protective group for an alcoholic hydroxyl group, and a process for preparing the 4-protected hydroxycyclopent-2-en-1-ones by oxidizing monohydroxy-protected derivatives of cyclopent-1-ene-3,5-diol expressed by the following formula

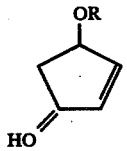

(1)

wherein R is the same as defined above. Optically active 4-hydroxycyclopent-2-en-1-one which is an optically active isomer of the compound of formula (2); or optically active cyclopent-1-en-3,5-diol (R-isomer) and a novel diacyl derivative of the diol, a novel monoacyl-monosilyl-derivative of the diol and a novel monoacyl-monotetrahydropyranol-derivative of the diol, which are intermediates for the protective derivative of formula (1). Processes are also provided for preparing the protective derivatives of formula (1) by converting these intermediates by esterification, hydrolysis, enzymatic processes, etc. The optically active compounds of formula (2) are useful as precursors for the preparation of prostaglandin or its analogues.

13 Claims, No Drawings

PROCESS FOR THE PREPARATION OF 4-HYDROXYCYCLOPENT-2-EN-1-ONE DERIVATIVES

This invention relates to new 4-hydroxycyclopent-2-en-1-one derivatives and a process for preparing same. More particularly, this invention relates to new 4-hydroxycyclopent-2-en-1-one derivatives, new intermediates from which said derivatives can be derived and a new process for their preparation.

In a typical process of this invention there is prepared from a monohydroxy protected derivative of a cyclopent-1-en-3,5-diol of the following formula (1)

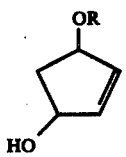

a 4-protected hydroxycyclopent-2-en-1-one of the following formula (2)

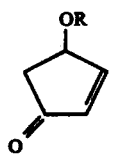

In the foregoing formulas (1) and (2), R represents an eliminatable alcoholic hydroxyl (—OH) protective group.

The monohydroxy protected derivatives of cyclopent-1-en-3,5-diols of the foregoing formula (1) include (i) the (R)-trans isomer of the following formula (1-1)

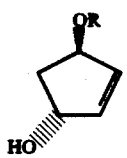

(ii) the (S)-trans isomer of the following formula (1-2)

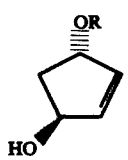

(iii) mixtures of optically active (R)-trans isomers and (S)-trans isomers in which one of either the foregoing (R)-trans isomer or (S)-trans isomer is contained in a greater proportion (This mixture will hereinafter be referred to as the optically active composition); and (iv) optically inactive racemic mixtures of the foregoing (R)-trans isomer and (S)-trans isomers (this mixture will hereinafter be referred to as the racemic mixture); as well as the cis isomers corresponding to the foregoing (i), (ii), (iii) and (iv) and mixtures of such cis isomers.

Therefore, unless otherwise indicated, the foregoing formula (1) is to be construed as inclusively representing all of these (i), (ii), (iii) or (iv) and the corresponding cis isomers thereof and cis isomer mixtures. Hereinafter, this method of representation will also be used in the case of the other compounds in which optical isomers are present.

The new 4-protected hydroxycyclopent-2-en-1-ones of this invention represented by the foregoing formula (2) are extremely valuable intermediates for the preparation of medicines, agricultural chemicals or perfumes.

For instance, the prostaglandin compounds have been attracting attention in recent years as being a substance exhibiting marked physiological activities such as the smooth muscle contraction activity, anti-inflammatory activity, gastric secretion inhibiting activity, hypotensive or hypertensive activity, etc. While the prostaglandins can be found widely distributed in the tissues of mammals and can also be isolated in small amounts from natural sources, it is insufficient to satisfy all the demands and thus must be synthesized. And thus numerous methods, both chemical and biochemical, for its synthesis have been actually attempted. However, since these methods of synthesis either used very expensive starting materials or had to proceed through a great number of processing steps in the case the starting material was inexpensive, they were not commercially satisfactory.

Recently, there has been suggested a method of synthesizing the prostaglandins, and especially the natural prostaglandins, in which the processing steps have been greatly reduced and moreover the prostaglandins are obtained in good yield. This method, which uses protected 4-hydroxycyclopent-2-en-1-one derivatives as the starting material and enables the desired prostaglandins to be obtained in good yield in one or two steps, is attracting attention as being an epochal method [*Tetrahydron* Letters, 1535 (1975)].

So far as we known, only the optically inactive 4-acetoxy- and 4-benzyloxy-cyclopent-2-en-1-one of the following formulas (a) and (b) are known heretofore as being compounds that can be used as the starting material for preparing the foregoing prostaglandins.

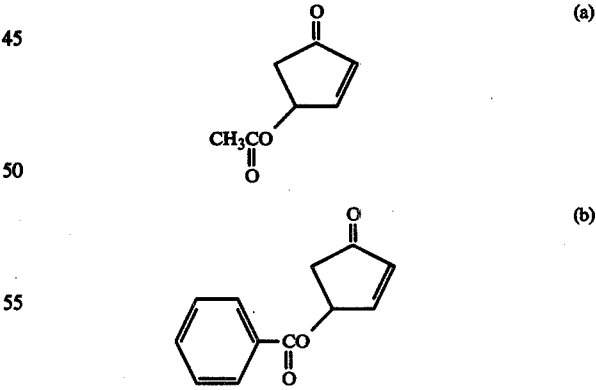

Further, the heretofore known processes for preparing the foregoing compounds (a) and (b) are exceedingly complicated. That is, in one process 2-cyclopentenone is brominated with N-bromosuccinimide (NBS) to form 4-bromocyclopent-2-en-1-one, after which this is reacted with silver acetate to prepare the 4-acetoxycyclopent-2-en-1-one of formula (a) [J. Org. Chem. 29, 3503 (1964)]. This process has the drawbacks that the yield of the 4-acetoxycyclopent-2-en-1-one by the bromination of the 2-cyclopentenone with NBS is low and, in addition, that the silver acetate is expensive. In the other conventional process, cyclopent-2-en-1-ol is benzoylated with benzoyl chloride to obtain 3-benzoyloxy-cyclopent-1-ene, which is reacted with NBS to obtain 3-benzoyloxy-5-bromocyclopent-1-ene, which is then oxidized with dimethyl sulfoxide (DMSO) to prepare the 4-benzoyloxy-cyclopent-2-en-1-one [*Helv. Chim. Acta* 53, 739 (1970)]. This process has the drawbacks that it involves a great number of processing steps and, in addition, the yield of the 4-benzoyloxy-cyclopent-2-en-1-one resulting from the oxidation step by the DMSO is low. Moreover, in the case where the hydroxy group in the 4-position is still in a state of protection by the acetyl or benzoyl group as in the foregoing formulas (a) and (b), the derivation of prostaglandins by the conventional processes [e.g., the process of the aforementioned *Tetrahydron Letters*, 1535 (1975)] is not possible.

It is therefore an object of this invention to provide a new process for preparing 4-protected hydroxy-cyclopent-2-en-1-ones and the intermediates therefor.

Another object of this invention is to provide optically active new 4-protected hydroxy-cyclopent-2-en-1-ones and new intermediates therefor.

A further object of this invention is to provide new 4-protected hydroxy-cyclopent-2-en-1-ones from which prostaglandins can be directly derived.

Other objects and advantages of the invention will become apparent from the following description.

The process of the present invention can be represented by the following reaction scheme.

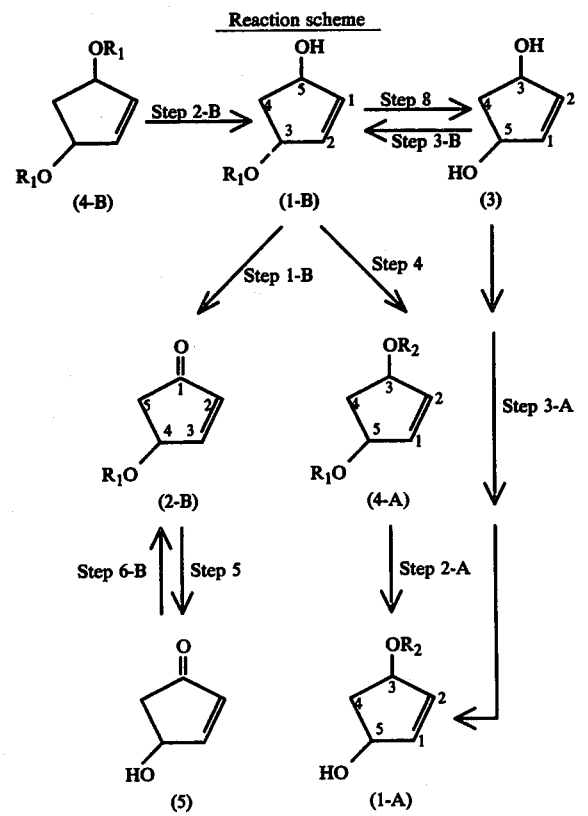

-continued
Reaction scheme

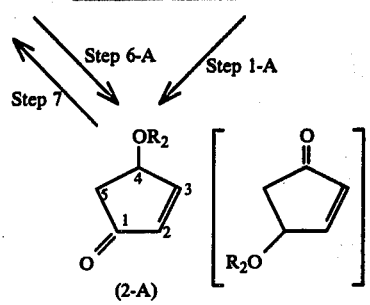

The process of this invention will be more fully described below.

[1] Step 1 (Steps 1-A and 1-B)

Step 1 of this invention, i.e., the procedures of Steps 1-A and 1-B in the foregoing reaction scheme, involves the process which comprises oxidizing the monohydroxy protected derivative of a cyclopent-1-en-3,5-diol of the following formula

wherein R is an eliminatable alcoholic hydroxyl (—OH) protective group, to prepare a 4-protected hydroxy-cyclopent-2-en-1-one of the following formula

wherein R is as above defined.

The protective group (R) in the foregoing formula (1) representing the starting material of Step 1 may be any protective group provided it is an alcoholic hydroxyl group (—OH) that can be eliminated. For example, convenient are such groups as trialkylsilyl groups, acyl groups of 2-11 carbon atoms, chain and cyclic alkoxyalkyl groups of 2-5 carbon atoms, benzyl groups or carbobenzyloxy groups. Further, as the foregoing trialkylsilyl groups, preferred are the trialkylsilyl groups having an alkyl group of 1-4 carbon atoms, and especially t-butyl-di-methylsilyl.

On the other hand, as the oxidizing agent to be used in Step 1, any of the usually known oxidizing agents of allyl alcohol, i.e., any which can convert the hydroxyl group of the allyl position to oxo group (O=) without oxidizing the double bond of the monohydroxy protected derivatives of the formula (1), can be used. As such an oxidizing agent, suitably used are especially 2,3-dichloro-5,6-dicyano-p-benzoquinone (DDQ), active manganese dioxide and the chromic acid-pyridine complex.

The oxidation reaction of Step 1 is preferably carried out in a solvent, and usuable as this reaction solvent are the inert organic solvents such as the ethers, aliphatic hydrocarbons, halogenated hydrocarbons and aromatic hydrocarbons. For example, when the aforesaid DDQ is used as the oxidizing agent, the use of dioxane is especially to be preferred, whereas when active manganese dioxide is used, the use of petroleum ether is to be preferred. The amount used of the solvent is imposed no particular restriction, and an amount of the order such as will suitably disperse the oxidizing agent used and permit stirring will suffice. Usually, 0.5 to 100 parts by weight, and preferably 1-20 parts by weight, of the solvent is used for each part by weight of the cyclopent-1-en-3,5-diol derivative used. While the reaction temperature to be used will depend upon the nature of the oxidizing agent used, usually a temperature in the range of -—30-100° C., and preferably 0-70° C., is employed. For example, when DDQ or active manganese oxide is used, especially preferred is a temperature ranging from room temperature (25° C.) to 70° C. The reaction time is determined by means of gas chromatography or thin-layer chromatography, the point at which the starting alcohol disappears being deemed as being the point at which the reaction has been completed. This usually takes from 3 to 60 hours. The proportion in which to use the oxidizing agent can be suitably chosen. While stoichiometrically 1.0 equivalent should be sufficient, preferably an amount of usually 1-6 equivalents is used for ensuring that the reaction is completely carried out.

After thus completing the reaction, the excess oxidizing agent is removed from the product, as by filtration, following which such usual procedures as extraction, distillation and chromatography are carried out to purify and obtain the product.

In the hereinbefore-described procedure of Step 1 of the present invention, the oxidation reaction per se is exactly the same in the case of Steps 1-A and 1-B, the division into the two Steps 1-A and 1-B being made in accordance with the class of the foregoing protective group (R) of formula (1), the formula for the starting material.

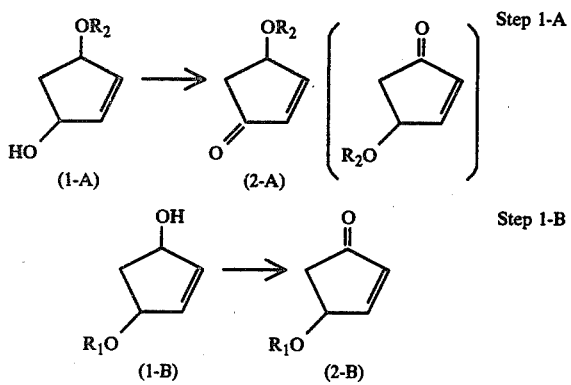

In the foregoing formulas, $R_2$ is an eliminatable ether-forming group such as the aforementioned trialkylsilyl groups, chain or cyclic alkoxyalkyl groups of 3-5 carbon atoms or benzyl groups; and $R_1$ is an eliminatable ester-forming group such as the aforementioned acyl groups of 2-11 carbon atoms or carbobenzyloxy groups. As the above $R_1$, the acetyl group ($CH_3CO—$) is especially suitable. On the other hand, as the above $R_2$, especially suitable are t-butyldimethylsilyl group, tetrahydropyranyl group and ethoxyethyl group, most to be preferred being the t-butyldimethylsilyl group.

As the foregoing 4-protected hydroxy-cyclopent-2-en-1-ones of formula (2-A) can be converted directly to the prostaglandins, they are especially useful in the present invention.

On the other hand, the 4-protected hydroxy-cyclopent-2-en-1-ones of formula (2-B) obtained in the foregoing Step 1-B cannot be directly converted to the prostaglandins, but, as shown in the foregoing reaction scheme, they must first be transformed to the foregoing compounds of formula (2-A) via the Steps 5 and 6, after which they can be converted to the prostaglandins.

For example, the new 4-protected hydroxy-cyclopent2-en-1-ones of formula (2-A) can be readily converted in a single or two-stage reaction to the compounds of the following formula (c).

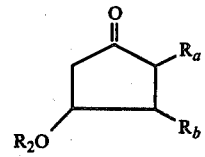

For example, when the $R_b$ in the compound (c) is a 3-hydroxyocto-1-enyl group and the $R_a$ is a 6-carboalkoxyhex-2-enyl group, the compound is an ester of prostaglandin $E_2$, which is noted for its strong physiological activity. Thus, it is seen that the new 4-hydroxycyclopent-2-en-1-one derivatives obtained by the invention process are exceedingly valuable as intermediates for medicines, agricultural chemicals or perfumes. The procedures of the aforesaid Steps 1-A and 1-B of this invention provide a method by which these new compounds can be obtained in good yield by a simple procedure. Hence, it is believed that the invention process is commercially of great value.

[2] The Starting Compounds of Step 1

2-1. The compounds of formulas (1-B) and (3)

The cyclopent-1-en-3,5-diol of formula (3), from which the 3-protected hydroxy-5-hydroxycyclopent-1-ene of formula (1-B), the starting material of the aforesaid Step 1-B, and the 3-protected hydroxy-5-hydroxycyclopent-1-ene, of formula (1-A), the starting material of Step 1-A, can be derived, can be prepared by various processes. These processes will be described below.

(1) A typical process is that disclosed in our copending patent application. According to this process, a diacyl ester of an optically active or inactive cyclopent-1-en-3,5-diol, preferably a dicetyl ester of said diol, of the following formula (d)

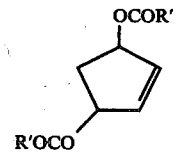

wherein R' is a monovalent hydrocarbon residue of 1-10 carbon atoms, the methyl group being especially preferred, is subjected to the action of a microorganism or enzyme having at least a selectivity in the hydrolysis rate between the acyloxy group of (R) configuration and the acyloxy group of (S) configuration, to prepare said optically active diacyl esters or the corresponding monoacyl esters or the optically active or inactive corresponding diols.

When, for example, a yeast of the Saccharomyces species, preferably baker's yeast, is used as this microorganism, at least one class of the following optically active compounds can be obtained.
(i) (R)-trans-diesters
(ii) (R)-trans-monoesters
(iii) (S)-trans-diols Further, when the treatment is carried out for a sufficiently prolonged period of time with these microorganisms, it is possible to obtain the optically inactive diols. Needless to say, the optically inactive diols can also be obtained by hydrolyzing said diacyl esters (d) with an alkali.

On the other hand, usable as the aforesaid enzymes are the hydrolytic enzyme contained in the rind of citrus fruits, the filamentous fungus belonging to the genus Aspergillus or the hydrolytic enzyme obtained from the metabolic product thereof. When a culture medium containing said diacyl esters (d) is inoculated with such enzymes, the following optically active compounds are accumulated in the culture medium.
(i) (S)-trans-diesters
(ii) (R)-trans-monoesters
(iii) 3(S)-acetoxy-5-(R)-hydroxy-cyclopent-1-ene These compounds can then be isolated and recovered from the culture medium.

On the other hand, when, for example, wheat germ lipase is used as the enzyme, the following optically active compounds can be obtained in similar manner.
(i) (R)-trans-diesters
(ii) (R)-trans-monoesters
(iii) 3(S)-acetoxy-5-(R)-hydroxy-cyclopent-1-ene Hence, the foregoing optically active (R)-trans-monoesters and 3(S)-acetoxy-5-(R)-hydroxy-cyclopent-1-ene obtained in the foregoing processes can be used as obtained as the starting material in the aforesaid Step 1-B of the present invention. On the other hand, the foregoing optically active or inactive diols can be used as the precursor [formula (3)] from which to derive the starting material of Step 1-A of this invention.

Further, the aforementioned optically inactive diacyl esters or the optically active (R)- or (S)-trans-diesters can be converted, say, by the procedure of Step 2-B of the foregoing reaction scheme to the starting material (1-B) of Step 1-B.

2-2. Step 2-B.

The foregoing optically inactive diacyl esters of cyclopent-1-en-3,5-diols can usually be converted to the corresponding monoesters [formula (1-B)] by hydrolyzing with an alkali or an acid. However, in the case of the foregoing optically active diacyl esters, there is generally a decline in the yield when they are converted to the corresponding optically active monoesters. Hence, the results obtained are undesirable.

On the other hand, it is possible in accordance with the present invention to readily convert the optically active or inactive foregoing diacyl esters to their corresponding monoesters in good yield when they are reacted with a compound having a hydroxyl group in the presence of a basic compound.

As the foregoing basic compound to be used as the catalyst in this step (Step 2-B) of the present invention, usable are the aliphatic or aromatic nitrogen-containing basic compounds. For example, preferably used are the amines such as n-propylamine, n-butylamine, n-amylamine, diethylamine, diisobutylamine and alpha-phenethylamine.

As the foregoing compound having a hydroxyl group, the alcoholic compounds are used. In the present reaction it is possible to permit this alcoholic compound to function as a solvent at the same time. Hence, it is preferred that it be one which is liquid at the reaction temperature. As compounds conveniently used for this purpose, mention can be made of the monohydric aliphatic alcohols such, for example, as methyl alcohol, ethyl alcohol, n-propyl alcohol, isopropyl alcohol, butanol and isobutyl alcohol.

The reaction, taking into consideration the stability of the reaction product, is carried out at a temperature in the range of 10-50° C., it usually being sufficient that the reaction be carried out at room temperature for 1-4 days. The nitrogen-containing basic compound, the catalyst, is used in an amount of 0.1-10 mols, and preferably 0.4-2 mols, based on the starting diester, whereas the compound having the hydroxyl group is used in an amount of at least 1.0 mol, and preferably 2-50 mols, based on said diester.

The reaction mixture obtained by a reaction such as hereinabove described usually consists of the unreacted starting diester, monoester and diol. For isolating the optically active trans-cyclopent-1-en-3,5-diol monoester (1-B) from this mixture, the usual procedure will suffice, an example of which will be described below.

The resulting reaction mixture is concentrated and then, after adding an organic solvent such as ether, washed with dilute hydrochloric acid, following which it is dried. This is followed by distilling off the solvent and then purifying the reaction mixture, if necessary, by such procedures as distillation and chromatography to obtain an optically active or inactive monoacyl ester of cyclopent-1-en-3,5-diol (1-B) of high purity.

For obtaining the corresponding foregoing optically active diols from the foregoing optically active diesters, this can be fully accomplished by, say, a hydrolysis reaction consisting of heating the foregoing diesters in methanol in the presence of preferably barium hydroxide or by the hereinafter-described reductive reaction of Step 2-A-1. It thus becomes possible to obtain (i) (R)-trans-cyclopent-1-en-3,5-diol of the formula

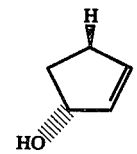

or an optically active diol containing the above diol in a higher concentration from the foregoing (R)-trans-diester or (R)-trans-monoester, or an optically active diester or monoester composition containing the above diester or monoester in a higher concentration and, on the other hand, (ii) (S)-trans-cyclopent-1-en-3,5-diol of the formula

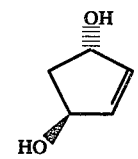

or an optically active diol containing the above diol in a higher concentration from the foregoing (S)-trans-diester or (S)-trans-monoester, or an optically active diester or monoester composition containing the above diester or monoester in a higher concentration.

2-3. Step 3-B

Further, the foregoing monoesters (1-B) can also be derived from the aforementioned optically active or inactive cyclopent-1-en-3,5-diols (Step 3-B).

In accordance with this invention, it was found that as the Step 3-B the aforesaid cyclopent-1-en-3,5-diols could be reacted with an acid halide or acid anhydride of an organic carboxylic acid in the presence of an organic nitrogen-containing basic compound of pKa 4–12 to convert said diols to optically active or inactive monoesters of cyclopent-1-en-3,5-diols (1-B) in good yield. The process for preparing the aforesaid optically inactive diols is described in, for example, Owen et al., J. Chem. Soc. 4035 (1952).

The organic carboxylic acid halides are preferred over the acid anhydrides in the foregoing reaction, and especially preferred is the use an organic monocarboxylic acid chloride or bromide of 1–10 carbon atoms. Acetyl chloride, acetyl bromide, benzoyl chloride and alpha-methoxy-alpha-trifluoromethylphenylacetyl chloride are particularly preferred.

On the other hand, as preferred examples of the aforesaid organic nitrogen-containing basic compounds of pKa 4–12, there can be named such compounds as pyridine, triethylamine, dimethylaniline, 2-ethylpyridine, 3-methylpyridine, 4-methylpyridine, 2,3-dimethylpyridine, 2,4-dimethylpyridine, 3,5-dimethylpyridine, collidine and imidazole.

The reaction is carried out in the presence or absence of a solvent. As the aforesaid organic nitrogen-containing basic compound also functions as a solvent, a solvent is not always necessary. However, when one is used, preferred are such nonprotonic polar solvents as dimethylformamide and dimethylacetamide, such aliphatic hydrocarbons as n-heptane and hexane, such ethers as dioxane, tetrahydrofuran and dimethoxyethane, such aromatic hydrocarbons as benzene, toluene and xylene, or the halogenated hydrocarbons. Of these solvents, especially preferred are the ethers.

When it is especially intended to prepare the monoesters in the above Step 3-B, the reaction is preferably carried out by dissolving a cyclopentene-3,5-diol in the solvent, after which an acid halide or acid anhydride is slowly added thereto while ensuring that the starting diol in the reaction system is maintained therein such as to be stoichiometrically in excess.

In this case, the reaction solvent is used in an amount of 1–100 parts by weight, and preferably 5–50 parts by weight, for each part by weight of the diol. On the other hand, in the case of the acid halide or acid anhydride, there also are preferably added after dissolving 1.0 part by weight thereof in not more than 50 parts by weight of the solvent.

A reaction temperature in the range of −20°–180° C., and especially 20°–40° C., is preferred.

On the other hand, as the organic nitrogen-containing basic compound, the use of one whose pKa is 5–11 is especially convenient.

For obtaining the monoesters in good yield, the addition of the acid halide or acid anhydride is best carried out slowly over a prolonged period of time. Thus, a dropwise addition time of 2–30 hours is preferably used.

While there are cases in which the product obtained in this step contains unreacted diol, monoester and diester, the intended monoester can be readily separated by such procedures as distillation, recrystallization, thin-layer chromatography and column chromatography.

While the foregoing monoacyl ester of formula (1-B) can be obtained by the present Step 3-B, it is possible by reacting the so obtained monoacyl ester further with an acylating agent having an acyl group differing from that of said monoacyl ester to obtain, for example, the new compounds (R)-trans-3-acetoxy-5[(+)-alpha-methoxy-alpha-trifluoromethylphenylacetoxy]cyclopent-1-ene of the following formula

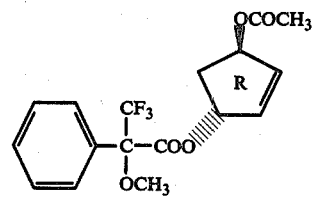

and (S)-trans-3-acetoxy-5-[(+)-alpha-methoxy-alpha-trifluoromethylphenylacetoxy]cyclopent-1-ene of the following formula

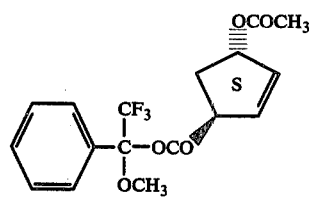

These compounds can be separated from each other, as by liquid chromatography, from a composition containing the two compounds in an optical proportion. Further, these compounds are suitable for determining their compositional ratio from the NMR of the composition.

2-4. Step 3-A

The 3-protected hydroxy-5-hydroxy-cyclopent-1-ene, the starting compound of the foregoing Step 1-A, is prepared via the following two routes:

(1) By the etherification (Step 3-A) of cyclopent-1-en-3,5-diol(3) or (2) By etherifying (Step 4) the aforesaid monoacyl ester of cyclopent-1-en-3,5-diol (1-B) followed by deacylation or elimination (Step 2-A) of the carbobenzyloxy.

The Step 3-A will now be described hereinafter.

In this Step 3-A the cyclopent-1-en-3,5-diol, while being maintained in a state of excess in the reaction system, is either 3-A-1. reacted with a trialkylsilyl chloride in an inert organic solvent in the presence of a base;

3-A-2. reacted with either a chain or cyclic vinyl ether of 3–5 carbon atoms in an inert organic solvent in the presence of a catalytic amount of an acid; or 3-A-3. reacted with a benzyl halide in an inert organic solvent in the presence of a base to thus prepare said 3-protected hydroxy-5-hydroxy-cyclopent-1-ene (1-A).

(1) Step 3-A-1

As the trialkylsilyl chloride to be used in the foregoing Step 3-A-1, t-butyldimethylsilyl chloride is especially suitable. On the other hand, as the inert organic solvent to be used in reacting such a silyl chloride, included are such inert solvents as the nonprotonic polar solvents, aliphatic hydrocarbons, aromatic hydrocarbons, halogenated hydrocarbons and ethers or the mixtures thereof. Of these, the use of such nonprotonic polar solvents as dimethylformamide and dimethyl sulfoxide is particularly desirable. The amount in which the solvent is used as imposed no particular restrictions, but when a nonprotonic polar solvent is used, it is preferred that the amount is not too great for obtaining the product by extraction after completion of the reaction. For example, the inert organic solvent is preferably used in an amount of 0.5-100 parts by weight, and especially 0.5-5 parts by weight, for each part by weight of the diol. While the reaction temperature can be suitably chosen, a temperature in the range of $-10°-+80°$ C. is favorably used for checking the decomposition of the trialkylsilyl chloride, especially preferred being a temperature in the neighborhood of room temperature (25° C.). While the proportion in which the trialkylsilyl chloride is suitably used is an amount equimolar to said diol from the stoichiometrical standpoint, an amount somewhat less than equimolar, i.e., 0.8-1.0 equivalent, is preferably used for obtaining the monoesters in a greater amount. The reaction time is determined by submitting the reaction product to, say, gas chromatography or thin-layer chromatography, the point at which the starting diol disappears being deemed the point at which the reaction has been concluded.

The proportion in which the monoether and diester, the products of the invention process, are formed can be controlled to a certain extent by the rate at which the trialkylsilyl chloride is added and the amount added thereof. For instance, the amount formed of the monoether can be increased as a general rule by retarding the rate at which the trialkylsilyl chloride is added and by using same at less than 1.0 equivalent of the diol.

On the other hand, as the basic compound, there can be named such compounds as, for example, pyridine, picoline, lutidine, triethylamine, tetramethylethylenediamine, triethylenediamine, N,N-dimethylaniline, 1,5-diazabicyclo[4,3,0]-5-nonene, 1,5-diazabicyclo[5,4,0]-5-undecene and imidazole. Of these basid compounds, especially preferred are, for example, pyridine when trimethylsilyl chloride is being used, and imidazole when t-butyldimethylsilyl chloride is being used.

Further, while a base is usually used as a reaction assistant in the invention reaction, most preferred is the use of imidazole as this base. And while it suffices to use the base in a proportion equimolar to the trialkylsilyl chloride, which is used in a stoichiometric amount, preferred is the use of 1.0-3.0 equivalents of the base.

The resulting product contains both the monoether and diether types of compounds, which two can be readily separated by thin-layer chromatography. Further, if necessary, the separated diether can be readily hydrolyzed and converted to the starting diol, which can again be used for obtaining the monoether.

On the other hand, as the trialkylsilyl chlorides to be used in this invention, such compounds as, for example, trimethylsilyl chloride, t-butyldimethylsilyl chloride, chloromethyldimethylsilyl chloride and bromomethyldimethylsilyl chloride are conveniently usable, of which t-butyldimethylsilyl chloride is especially to be preferred. Usable also are dimethylphenylsilyl chloride and triphenylsilyl chloride.

As previously stated, the cyclopent-1-en-3,5-diols used in the present step include not only those which are optically inactive but also those which are optically active. And the procedure for directly obtaining the optically active cyclopent-1-en-3,5-diols has already been described in section 2-1, above.

Further, the optical isomers such as (i) (R)-trans-diesters, (ii) (R)-trans-monoesters, (iii) (S)-trans-diesters and 3(S)-acetoxy-5(R)-hydroxy-cyclopent-1-ene mentioned in section 2-1, above, or the diester and monoester compositions containing such optical isomers in a higher concentration can all be converted, as hereinbefore indicated, to their corresponding optically active diols by the known hydrolytic procedure using either an alkali or an acid, preferably a procedure of reacting the foregoing optical isomers or compositions with a compound having a hydroxyl group in the presence of a basic compound, as described in the foregoing Step 2-B of section 2-2, above, or a procedure of subjecting the foregoing optical isomers or compositions to the action of microorganisms or enzymes.

Hence, if optical isomers of diols corresponding to the foregoing (i), (ii), (iii) or (iv) or optically active compositions containing these in higher concentrations are used as the starting material in the aforesaid Step 3-A-1, the 3-trialkylsiloxy-5-hydroxy-cyclopent-1-enes corresponding thereto can be obtained by the hereinbefore-described trialkylsilylation procedure.

We believe the optically active or inactive 3-trialkylsiloxy-5-hydroxy-cyclopent-1-enes obtained in this step are new compounds, and that we were the first to secceed in their synthesis and isolation.

Of these new compounds, the mono-t-butyldimethylsilyl ether of (R)-trans-cyclopent-1-en-3,5-diol of the following formula

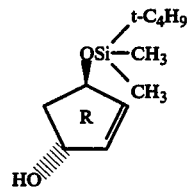

and the mono-t-butyldimethylsilyl ether of (S)-trans-cyclopent-1-en-3,5-diol of the following formula

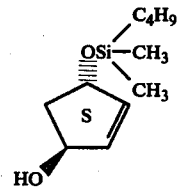

are especially valuable as optically active intermediates from which can be derived the prostaglandins (2) Step 3-A-2

The chain or cyclic vinyl ethers of 3-5 carbon atoms to be used in Step 3-A-2 include, for example, ethyl vinyl ether, ethyl isopropyl ether and dihydropyran, of which dihydropyran is especially suitable. On the other hand, as the aforesaid inert organic solvent to be used in carrying out the reaction of such vinyl ethers, usable are those inert organic solvents mentioned in the foregoing Step 3-A-1, of which especially preferred are the halogenated hydrocarbons and ethers. While there is imposed no particular restriction as to the amount in which the solvent is used, preferred is, for example, an amount in the range of 0.5-100 parts by weight, and particularly 0.5-10 parts by weight, for each part by weight of the aforesaid diol. The reaction temperature is −10°-+50° C., and preferably 0°-30° C. While the reaction time will vary depending upon the reaction conditions, a reaction time of from 30 minutes to 10 hours will usually be sufficient. The vinyl ether is preferably used in a proportion of 0.8-1.2 mols, and particularly 0.9-1.0 mol, for each mol of said diol. As the acid used as the reaction assistant, mention can be made of such acids as p-toluenesulfonic acid, hydrochloric acid and sulfuric acid, of which most to be preferred is p-toluenesulfonic acid. Its use in a catalyst amount (not more than several %) will be sufficient. The 3-protected hydroxy-5-cyclopent-1-enes (1-A) can be readily separated from the resulting reaction product by submitting the latter to such procedures as distillation, column chromatography and thin-layer chromatography.

Hence, it is possible in this Step 3-A-2 to obtain as in the foregoing Step 3-A-1 the optically active 3-protected hydroxy-5-hydroxy-cyclopent-1-enes by using the optically active diols as the starting material. These optically active 3-protected hydroxy-5-hydroxy-cyclopent-1-enes are also new compounds.

Of these compounds, the monotetrahydropyranyl ether of (R)-trans-cyclopent-1-en-3,5-diol of the following formula

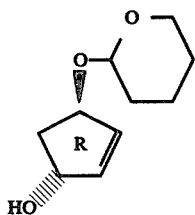

and monotetrahydropyranyl ether of (S)-trans-cyclopent-1-en-3,5-diol of the following formula

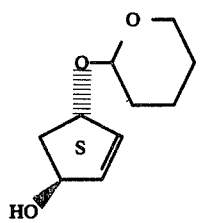

are especially of great value as new optically active intermediates from which can be derived the prostaglandins.

(3) Step 3-A-3

In this Step 3-A-3, as the benzyl halide to be used therein, mention can be made of benzyl chloride and benzyl bromide. These are used in an amount of 0.8-2.0 mols, and preferably 0.9-1.5 mols, for each mol of said starting diol. As the aforesaid inert organic solvent, those mentioned in Step 3-A-1, above, can be used, of which especially preferred are the aromatic hydrocarbons and ethers. These solvents are used in an amount of preferably 0.5-100 parts by weight, and more preferably 0.5-50 parts by weight, for each part by weight of the diol. In carrying out the reaction, first, 1.0 mol of the diol is reacted with 0.8-1.2 mols, and preferably 0.9-1.1 mols, of a base in the inert organic solvent to obtain an alkoxide of said base, after which the benzyl halide is added thereto, the addition of the latter being preferably carried out in as gradual a manner as possible. Usable as the base in this case are preferably such compounds as sodium hydride, potassium hydride, potassium t-butoxide and n-butyl lithium. The reaction is carried out at a temperature of −30°-100° C., and preferably 0°-80° C. While the reaction time will vary depending upon the reaction condition, a period of time of the order of several hours will be sufficient. The 3-protected hydroxy-5-hydroxy-cyclopent-1-enes (1-A) can be readily separated from the resulting reaction product by submission to such procedures as distillation, column chromatography and thin-layer chromatography.

It is thus also possible in this Step 3-A-3 by using the optically active cyclopent-1-en-3,5-diols to obtain as in the instances previously described the corresponding optically active 3-benzyloxy-5-hydroxy-cyclopent-1-enes. All of these optically active compounds are also new compounds.

The monobenzyl ether of (R)-trans-cyclopent-1-en-3,5-diol of the following formula

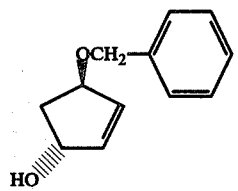

and the monobenzyl ether of (S)-trans-cyclopent-1-en-3,5-diol of the following formula

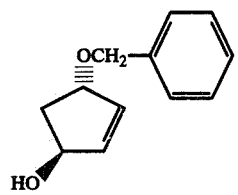

that are obtained in this step are also new compounds that are valuable as optically active intermediates from which can be derived the prostaglandins.

However, in this invention, the monotrialkylsilyl ethers and monotetrahydropyranyl ethers described in the foregoing Steps 3-A-1 and 3-A-2 are also valuable as such intermediates.

(4) Again Regarding Step 1-A

Therefore, when the oxidation reaction described in the hereinbefore-described Step 1 (Step 1-A) is carried out, using as the starting compounds the optically active 3-protected hydroxy-5-hydroxy-cyclopent-1-enes described in 3-A-1, 3-A-2 and 3-A-3, above, the corresponding optically active new 4-protected hydroxy-cyclopent-2-en-1-ones are obtained.

Thus, it is possible in accordance with Step 1 (Step 1-A) of the present invention to prepare (R)-4-(t-butyldimethylsiloxy)-cyclopent-2-en-1-one of the following formula

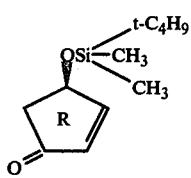

(S)-4-(t-butyldimethylsiloxy)-cyclopent-2-en-1-one of the following formula

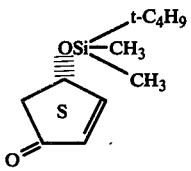

(R)-4-(tetrahydropyranyloxy)-cyclopent-2-en-1-one of the following formula

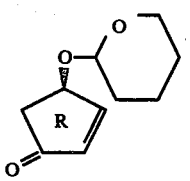

and (S)-4-(tetrahydropyranyloxy)-cyclopent-2-en-1-one of the following formula

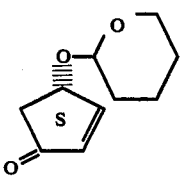

or optically active compositions containing such new optically active isomers in a higher concentration.

All of these optically active isomers and optically activ compositions are useful precursors for preparing the prostaglandins.

[3] Step 4 and Step 2-A

That the 3-protected hydroxy-5-hydroxy-cyclopent-1-enes (1-A), the starting compounds of the foregoing Step 1-A, can not only be prepared by the aforesaid Step 3-A but also via Steps 4 and 2-A using as the starting material the aforementioned monoacyl esters of cyclopent-1-en-3,5-diols (1-B) is as indicated at the beginning of the section 2-4, wherein Step 3-A is described. Accordingly, these Steps 4 and 2-A will now be described below.

3-1. Step 4

An optically active or inactive monoacyl ester of cyclopent-1-en-3,5-diol of the following formula 1-B

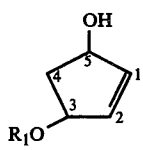

obtained by such procedures as described in sections 2-1 (the procedure wherein microorganisms or enzymes are used), 2-2 (Step 2-B) or 2-3 (Step 3-B), above, is used as the starting material, to which one of the following etherification procedures described in Step 3-A, above, is applied, i.e.:

3-A-1. A procedure of reacting the starting monoacyl ester with a trialkylsilyl chloride in an inert organic solvent in the presence of a base;

3-A-2. A procedure of reacting the monoacyl ester with a chain or cyclic vinyl ether of 3–5 carbon atoms in an inert organic solvent in the presence of a catalytic amount of an acid; or 3-A-3. A procedure of reacting the monoacyl ester with a benzyl halide in an inert organic solvent in the presence of a base; to form a 3,5-di-protected hydroxy-cyclopent-1-ene of the following formula 4-A

wherein $R_1$ is an eliminatable ester-forming group such as an acyl group of 2–11 carbon atoms or a carbobenzyloxy group, and $R_2$ is an eliminatable ether-forming group such as the foregoing trialkylsilyl group, a chain or cyclic alkoxyalkyl group of 3–5 carbon atoms or a benzyl group.

In this reaction, the hydroxyl group (—OH) in the 5-position is protected by the protective group ($R_1$). Hence, there is no necessity in the etherification reaction of maintaining the starting monoacyl ester such that it is contained in excess in the reaction system, and the 3,5-di-protected hydroxy-cyclopent-1-enes of the above formula 4-A can be formed by any of the foregoing procedures 3-A-1, 3-A-2 and 3-A-3.

As the foregoing monoacyl esters of formula (1-B), there can be named such, for example, as 3-hydroxy-5-acetoxy-cyclopent-1-ene, 3-hydrocy-5-benzoyloxycyclopent-1-ene, 3-hydroxy-5-propionyloxycyclopent-1-ene and 3-hydroxy-5-alphamethoxy-alpha-trifluoromethylphenylacetoxycyclopent-1-ene.

As previously indicated, these monoacyl esters give not only the optically active racemic mixtures but also such optically active isomers as, especially, (i) (R)-trans monoesters, (ii) (S)-trans monoesters, or (iii) 3(S)-acyloxy-5-(R)-hydroxy-cyclopent-1-ene, or the optically active monoester compositions containing at least one of these isomers in a higher concentration.

Hence, when these optically active isomers or an optically active composition containing these optically active isomers in a higher concentration is used as the starting material in the above-described Step 4, the corresponding optically active 3,5-di-protected hydroxy-cyclopent-1-enes are formed. As the etherification agent, those previously indicated in Steps 3-A-1, 3-A-2 and 3-A-3 as being suitable are likewise suitable in this case.

The separation and purification of the reaction product of Step 4 can be carried out in the following manner. After adding either water or an aqueous electrolytic solution to the reaction mixture, the extraction of the intended product is carried out by treating with an ether such as diethyl ether, a saturated hydrocarbon such as petroleum ether or hexane, an aromatic hydrocarbon such as benzene or toluene, or a halogenated hydrocarbon such as methylene chloride or chloroform. The resulting organic layer is first washed with an acidic water or an aqueous electrolytic solution in the case where a base has been used in the reaction of the foregoing Step 4, or with an alkaline water or an aqueous electrolytic solution in the case where an acid has been used in said reaction. Next, thorough washing of the organic layer is carried out with either neutral water or an aqueous electrolytic solution, after which it is dried with anhydrous sodium sulfate and thereafter concentrated to obtain the crude product. When it is desired to carry out further purification of the so obtained crude product, it can be submitted to distillation, column chromatography or preparative thin-layer chromatography, whereby a high-purity 3,5-di-protected hydroxycyclopent-1-ene of the foregoing formula (4-A) can be obtained.

The optically active or inactive 3,5-di-protected hydroxy-cyclopent-1-enes of formula (4-A) obtained by the process of this invention are, so far as we know, all new compounds.

Of these compounds that are obtained by this Step 4, the following compounds, for example, the (R)-trans-3-acetoxy-5-t-butyldimethylsiloxy-cyclopent-1-ene of the following formula

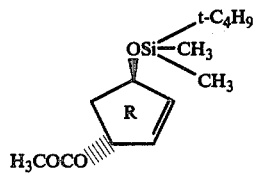

(S)-trans-3-acetoxy-5-t-butyldimethylcyclopent-1-ene of the following formula

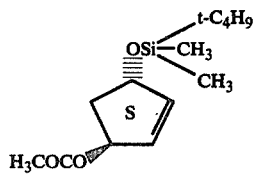

(R)-trans-3-acetoxy-5-tetrahydropyranyloxycyclopent-1-ene of the following formula

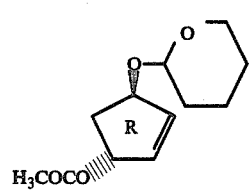

and (S)-trans-3-acetoxy-5-tetrahydropyranyloxycyclopent-1-ene of the following formula

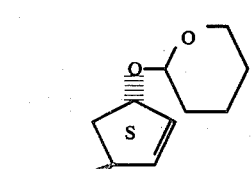

are all valuable new optically active intermediates from which can be derived the prostaglandins.

Further, the following compounds obtained by Step 4, for example, (R)-trans-3-t-butyldimethylsiloxy-5-[(+)-alpha-methoxy-alpha-trifluoromethyl-phenylacetoxy]cyclopent-1-ene of the following formula

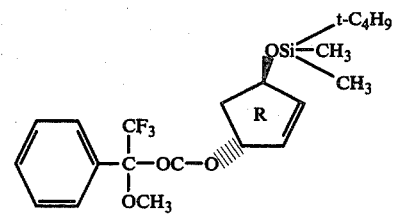

and (S)-trans-3-t-butyldimethylsiloxy-5-[(+)-alpha-methoxy-alpha-trifluoromethylphenylacetoxy]cyclopent-1-ene of the following formula

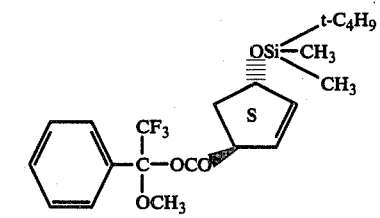

can be converted to the compounds of formula (1-A) in their as-obtained state, or after separation from each other by, say, liquid chromatography, by the hereinafter-described Step 2-A. Thus, the foregoing compounds can be utilized as a mixture of the (R)-trans isomer and (S)-trans isomer, or after their separation, for the determination of the configuration of the 3,5-dihydroxycyclopentene derivatives or the determination of the composition of the optical isomers, as well as for the method of separating these optical isomers. Hence, these compounds are extremely useful.

3-2. Step 2-A

The foregoing 3,5-di-protected hydroxy-cylopent-1-enes of formula (4-A) obtained by the above-described Step 4 can be converted to the 3-protected hydroxy-5-hydroxycyclopent-1-enes of the following formula

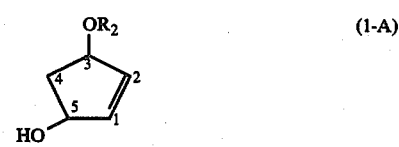

by either of the following procedures, i.e.,

Step 2-A-1. By reduction or hydrolysis; or

Step 2-A-2. By submitting the foregoing compounds to the action of an enzyme having the ability of hydrolyzing the acyl group or the carbobenzyloxy (ester group).

Of these two procedures, the foregoing compounds of formula (1-A) can generally be obtained in higher yields by the procedure of Step 2-A-1 than by that of Step 2-A-2. As regards the foregoing 3-protected hydroxy-5-hydroxy-cyclopent-1-enes of formula (1-A), these have already been fully described in Step 3-A.

(1) Step 2-A-1

In this Step 2-A-1 the deacylation of the foregoing 3,5-di-protected hydroxy-cyclopent-1-enes of formula (4-A) is carried out by the reduction or hydrolysis of same using a suitable reducing agent or a suitable hydrolytic assistant in an inert medium in preferably an atmosphere of an inert gas.

Such gases as nitrogen and argon are used as the inert gas, while usable as the inert medium are the saturated hydrocarbons such, for example, as pentane, hexane, heptane and cyclohexane; the aromatic hydrocarbons such, for example, as benzene, toluene and xylene; the halogenated hydrocarbons such, for example, as methylene chloride, chloroform and carbon tetrachloride; the ethers such, for example, as diethyl ether, tetrahydrofuran, dioxane, dimethoxyethane, diethylene glycol and dimethyl ether; and the nonprotonic polar solvents other than those mentioned above such, for example, as dimethylformamide, dimethylacetamide, hexamethylphosphoric triamide, N-methylpyrrolidone and dimethyl sulfoxide. These media can be used either singly or as a mixture of two or more thereof. While there is imposed no particular restriction as to the amount in which the medium is used, it is usually used in an amount of 0.5 to 1000 mols, and more preferably 10 to 100 mols, for each mol of the foregoing starting material of formula (4-A).

As the reducing agent to be used, mention can be made of such, for example, as aluminum hydride, diisobutylaluminum hydride, lithium aluminum hydride, sodium aluminum hydride and lithium borohydride, of which lithium aluminum hydride is especially preferred. It will suffice to use the reducing agent in an amount of 0.8 to 50 equivalents, and more preferably 1.0 to 10 equivalents, for each mol (equivalent) of the foregoing starting material of formula (4-A). While the reaction temperature to be used in this case will vary depending upon the reducing agent used, a temperature in the range of $-78°$ to $100°$ C., and more preferably $0°$ to $60°$ C. is used. The reaction time will also vary greatly depending upon the reducing agent used and the reaction temperature. However, when, say, lithium aluminum hydride is used, a reaction time of 30 minutes to 2 hours should be sufficient.

On the other hand, as the hydrolytic assistant of the ester group, a great number of both the acidic and basic catalysts are known. While any of these may be used, especially preferred is barium hydroxide. The use of the hydrolytic assistant in an amount ranging from the catalytic amount to 10 equivalents for each mol (equivalent) of the starting material of formula (4-A) will do. While the reaction temperature to be used in this case will vary depending upon the hydrolytic assistant used, one in the range of $-78°$ to $100°$ C., and preferably $0°$ to $60°$ C., will do. The reaction time will also vary greatly depending upon the hydrolytic assistant used and the reaction temperature. However, when, say, barium hydroxide is used, heating under reflux for 10 minutes to one hour in methanol should be sufficient.

The end point of both the reductive deacylation reaction and the hydrolytic deacylation reaction can be determined by following the progress of the reaction using either thin-layer chromatography or gas chromatography. Again, such a method of determining the end point is desirable.

The separation and purification of the so obtained 3-protected hydroxy-5-hydroxy-cyclopent-1-ene is then carried out in the following manner. First, if desired, the media such as methanol are distilled off under reduced pressure. Water or an aqueous electrolytic solution is then added to the reaction mixture, after which the intended product is extracted, using such ethers as diethyl ether, such saturated hydrocarbons as petroleum ether and hexane, such aromatic hydrocarbons as benzene and toluene and such halogenated hydrocarbons as methylene chloride and chloroform. The resulting organic layer is thoroughly washed in water or an aqueous electrolytic solution, dried with anhydrous sodium sulfate and thereafter concentrated to obtain a crude product. When this crude product is submitted as in Step 3-A, above, to distillation, column chromatography or preparative thin-layer chromatography, it can be converted to an optically active or inactive high purity 3-protected hydroxy-5-hydroxycyclopent-1-ene of formula (1-A).

Again, as already indicated previously, this optically active or inactive 3-protected hydroxy-5-hydroxy-cyclopent-1-ene of formula (1-A) can be converted to the corresponding optically active or inactive 4-protected hydroxy-cyclopent-2-en-1-one by the hereinbefore-described method of Step 1 (Step 1-A).

(2) Step 2-A-2

It is also possible to produce the 3-protected hydroxy-5-hydroxy-cyclopent-1-enes of formula (1-A) by subjecting the 3,5-di-protected hydroxy-cyclopent-1-enes of formula (4-A) to the action of enzymes having the ability of hydrolyzing the ester group (acyl or carbobenzyloxy group) of the latter.

Suitably usable as such enzymes are, for example, the esterases such as citrus esterase.

In these enzymatic reactions, any of such enzymes as the enzyme product obtained by the usual method of purifying enzymes, the crude product obtained by fractionation with ammonium sulfate or an organic solvent, or the unpurified product can be used. On the other hand, as the reaction solution, deionized water or an aqueous solution that can maintain the activity of the enzymes, such as a buffer solution, can be used.

For example, as the buffer solution, there are those mentioned in *Nogei Kagaku Jikkensho*, vol. 2, edited by the Department of Agricultural Chemistry, College of Agriculture, Kyoto University, pages 670–677. While as the ion concentration of the buffer solution one which makes it possible for the enzymatic activity to take place substantially will do, preferred is that in the range of $1 \times 10^{-5}$–5 mols. On the other hand, the pH of the reaction solution is also one which makes it possible for the enzymatic activity to take place substantially. Especially preferred is however that which is in the range of $\pm 2.0$ centering about the optimum pH of the enzyme used.

While the concentration of the substrate used is that which makes it possible for the enzymatic activity to take place substantially, preferred is a concentration of the order of $1 \times 10^{-4}$–25% by weight based on the reaction solution, especially preferred being that of the order of $1 \times 10^{-3}$–5% by weight.

A reaction time, say, of about 6–12 hours is preferred, but especially preferred is a time of 12–72 hours. While as the reaction temperature any will do as long as it is a temperature which makes it possible for the enzymatic reaction to take place, preferred is a temperature of 25–45° C.

The isolation of the product can be readily carried out by such usual procedures as that of extracting the product with an organic solvent or that of separating the product by means of column chromatography using an ion-exchange resin or synthetic adsorbing resin. For instance, the product can be extracted from the reaction solution with the usual organic solvents such as, for example, as ethyl acetate, ether, chloroform, benzene, hexane, cyclohexane, etc., following which an aftertreatment such as distilling off of the solvent is carried out in customary manner to readily obtain the crude product.

This crude product can be further purified by the same method of purification as that described in Step 2-A-1, above. Further, the optically active or inactive 3-protected hydroxy-5-hydroxy-cyclopent-1-ene obtained by the above method can also be converted to its corresponding active or inactive 4-protected hydroxy-cyclopent-2-en-1-one by the procedure of Step 1 (Step 1-A).

[4] Step 5

When the optically active or inactive 4-protected hydroxy-cyclopent-2-en-1-one of the following formula (2-B)

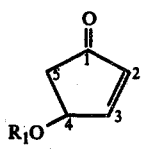
(2-B)

wherein $R_1$ is an eliminatable ester-forming group such as an acyl group of 2–11 carbon atoms or a carbobenzyloxy group, obtained in Step 1 (Step 1-B), above, is subjected to the action of an enzyme having the ability of hydrolyzing the ester group ($R_1$) thereof, the corresponding optically active or inactive 4-hydroxy-cyclopent-2-1-one of the following formula (5)

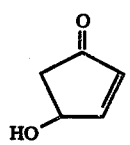

is obtained (Step 5).

The enzymes to be used in this Step 5 are those which can hydrolyze the esters. For example, most suitable are such enzymes as lipase. As specific examples, the wheat germ lipase (glycerol-ester hydrolase EC No. 3.1.1.3) or the hydrolytic enzyme prepared from *Aspergillus niger* ATCC 9142 are conveniently used.

The enzymatic reaction of this Step 5 can be carried out under identical conditions as in the case of Step 2-A-2, above. Again, the separation and purification of the crude product can also be carried out by the same procedures as described in Step 2-A-2, above.

It thus becomes possible in accordance with this invention to use either (i) the (R)-trans-monoester or (ii) the (S)-trans-monoester of the foregoing cyclopent-1-en-3,5-diols of formula (1-B) and by applying the Steps 1-B and 5 to prepare the corresponding (R)-4-hydroxycyclopent-2-en-1-one of the following formula

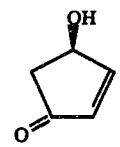

and (S)-4-hydroxycyclopent-2-en-1-one of the following formula

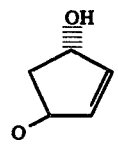

[5] Step 6-A

When the 4-hydroxycyclopent-2-en-1-one obtained in the foregoing Step 5 is etherified in accordance with the Steps 3-A-1, 3-A-2 or 3-A-3, above, the hereinbefore-described compound of the following formula (2-A)

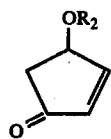

wherein $R_2$ is an eliminatable ether-forming group such as a trialkylsilyl group, a chain or cyclic alkoxyalkyl group of 3–5 carbon atoms or a benzyl group, can be prepared (Step 6-A).

In the process of this Step 6-A, especially suitable are the trialkylsilyl etherification of Step 3-A-1, above, and the etherification using vinyl ether of Step 3-A-2, above. The same reaction conditions and method of separation and purification of the product as those used in Steps 3-A-1 and 3-A-2 can be used.

[6] Step 7

On the other hand, when optically active or inactive 4-protected hydroxy-cyclopent-2-en-1-one of the following formula (2-A)

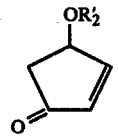
(2-A)

wherein $R_2'$ is a trialkylsilyl or a chain or cyclic alkoxyalkyl group of 3–5 carbon atoms, prepared by Step 1-A or Step 6-A, above, is contacted with an acidic aqueous or alcoholic medium, the corresponding optically active or inactive 4-hydroxy-cyclopent-2-en-1-one of the following formula (5)

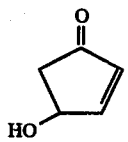
(5)

can be formed (Step 7).

When the foregoing $R_2'$ is a trialkylsilyl group, an acidic aqueous solution is suitably used in this case. On the other hand, when the $R_2'$ is the foregoing alkoxyalkyl group, either an acidic aqueous or an alcoholic medium can be used.

While the organic carboxylic acids are especially preferred as the acidic aqueous solution, such other organic acids as the organic sulfonic acids or the inorganic acids can likewise be used.

The organic carboxylic acids include, for example, such acids as formic acid, acetic acid, propionic acid, butyric acid and isobutyric acid, of which acetic acid is especially preferred.

When an aqueous medium is used as the reaction system, the reaction proceeds more smoothly when an organic solvent is added to the reaction system. As such organic solvents, preferably used are those which are soluble in water and of low boiling point such, for example, as dioxane, dimethoxyethane and tetrahydrofuran. On the other hand, as the alcoholic medium, conveniently used are such, for example, as methanol and ethanol.

The proportion in which the acid is used greatly affects the progress of the reaction. For instance, when an organic acid is used, it is preferred that the proportion of the organic acid be not greater than 70% by weight or that the proportion of the water and the organic solvent be at least 30%. Especially, when the $R_2'$ is a trialkylsilyl group, a convenient acidic aqueous solution is that whose weight ratio of acetic acid:water:-tetrahydrofuran is 3:1:1. And such an acidic aqueous solution preferably is used in a proportion of 0.5–100 parts by weight, and especially 1–10 parts by weight, per each part weight of the foregoing starting material of formula (2-A). A reaction temperature of $-30\text{--}100°$ C., and especially 0–50° C., is conveniently used.

The 4-hydroxycyclopent-2-en-1-one of formula 5 obtained by this reaction is relatively instable under thermal as well as acidic conditions. Hence, it is preferred that the reaction temperature, as indicated above, be as low as possible. The progress of the reaction can be detected by thin-layer chromatography, and that point at which the starting material disappears can be deemed to be the point at which the reaction is concluded. In general, it takes 40–60 hours for the reaction to be completed. In view of the fact that the affinity of the intended product for water is exceedingly great, its isolation can be carried out readily by extracting the reaction mixture by salting it out with an organic solvent and thereafter distilling off the solvent. Further, as another method, the crude product can be obtained by adding to the reaction system a solvent such as benzene, toluene or acetonitrile and thereafter azeotropically distilling off the solvent under reduced pressure, after which the resulting crude product can be purified by column chromatography or thin-layer chromatography.

Thus, an optically active or inactive 4hydroxycyclopent-2-en-1-one of formula (5) can be prepared in accordance with the invention process.

[7] Step 6-B

Therefore, the optically active or inactive 4-hydroxycyclopent-2-en-1-one prepared by the Step 7 or 5 is represented by the following formula (5)

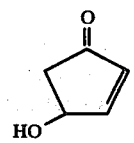

(5)

On acylation or carbobenzyloxylation of the 4-hydroxycyclopent-2-en-1-one, there can be formed the corresponding optically active or inactive 4-protected hydroxy-cyclopent-2-en-1-ones of the following formula (2-B)

(2-B)

wherein $R_1$ is an acyl group of 2–11 carbon atoms or a carbobenzyloxy group.

The process of this Step 6-B can be carried out more conveniently by acylation using an acid halide instead of an acid anhydride. Conveniently usable as the acid halides are such compounds as acetyl chloride, acetyl bromide, propionic acid chloride, propionic acid bromide, chloroacetyl chloride, benzoyl chloride and alpha-methoxy-alpha-trifluoromethylphenylacetyl chloride.

As there is only one hydroxyl group to be acylated in this reaction, the 4-hydroxycyclopent-2-en-1-one, the starting material, need not be maintained in excess in the reaction system. Except for this point, the 4-protected cyclopent-2-en-1-ones of formula (2-B) can be formed by the hereinbefore-described Step 3-B. That is to say, the same reaction conditions and methods of separation and purification as those described in the aforesaid Step 3-B can be employed.

Of the foregoing 4-protected hydroxy-cyclopent-2-en-1-ones of formula (2-B) thus obtained in accordance with the present invention, the following compounds, for example, (R)-4-acetoxycyclopent-2-en-1-one of the following formula (S)-4-acetoxycyclopent-2-en-1-one of the following formula (R)-4-benzoyloxycyclopent-2-en-1-one of the following formula

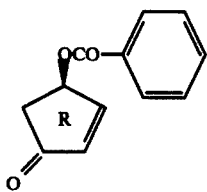

and (S)-4-benzoyloxycyclopent-2-en-1-one of the following formula

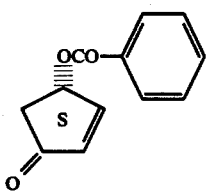

and of which especially the 4-benzoyloxy isomers are compounds that are useful for determining the absolute configuration. Again, the following compounds obtained by this step, for example, (R)-4-[(+)-alpha-methoxy-alpha-trifluoromethylphenylacetoxy]cyclopent-2-en-1-one of the following formula

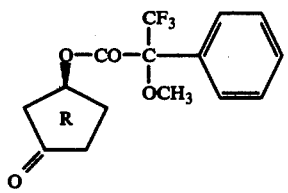

and (S)-4-[(+)-alpha-methoxy-alpha-trifluoromethylphenylacetoxy]cyclopent-2-en-1-one of the following formula

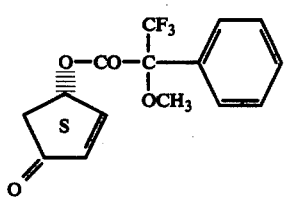

are new compounds which can be readily separated especially from each other by, say, liquid chromatography from a composition containing the two compounds in an optical proportion. Further, these are new compounds which are convenient for determining from the NMR of their composition the proportion in which each are contained.

EXAMPLE 1

Preparation of compound (1-B) by Step 3-B

Preparation of 3-actoxy-5-hydroxycyclopent-1-ene 0.70 gram (7.0 mmols) of 3,5-dihydroxycyclopent-1-ene and 0.83 gram (10.5 mmols) of pyridine were dissolved in 20 milliliters of anhydrous tetrahydrofuran, after which a solution of 0.70 g (9.0 mmols) of acetic acid chloride in 6 milliliters of anhydrous tetrahydrofuran was added dropwise over a period of 15 hours at room temperature in a stream of dried nitrogen, using a syringe drive. After concentrating the solvent with a rotary evaporator, 20 milliliters of ethyl acetate was added, following which the reaction mixture was washed with dilute hydrochloric acid (5 ml × 2), saturated sodium bicarbonate solution (5 ml × 2) and saturated sodium chloride solution (5 ml × 2). The organic layer was then separated and dried with anhydrous sodium sulfate. On distilling off the solvent, 1.00 gram of a colorless oil substance was obtained.

When a part of the so obtained substance was analyzed by gas chromatography, the yields of 3-acetoxy-5-hydroxycyclopent-1-ene and 3,5-diacetoxycyclopent-1-ene were 68% and 25%, respectively.

Further, this substance was submitted to thinlayer chromatography (developing solvent: a 4:6 n-hexane/ethyl acetate mixture) and separated into a monoacetate and a diacetate of Rf = 0.29 and Rf = 0.51. This monoacetate was submitted to separative gas chromatography and separated into two components (M-1 and M-2) exhibiting respectively the following properties.

M-1

IR (liquid film, cm$^{-1}$):
 3350, 1725, 1255, 1060, 1020.
NMR (CDCl$_4$, δ(ppm)):
 1.62 (dt, J = 4.0, 14.0 Hz, 1H),
 2.80 (dt, J = 7.0, 14.0 Hz, 1H),
 2.04 (s, 3H), 2.70 (bs, 3H),
 4.62–4.84 (m, 1H),
 5.40–5.60 (m, 1H),
 5.96, 6.12 (2dm, J = 5 Hz, 2H).
Mass (m/e):
 142 (M$^+$), 126, 125, 100, 99, 82, 43.

M-2

IR (liquid film, cm$^{-1}$):
 3350, 1720, 1260, 1055, 1025, 850, 810, 760.
NMR (CDCl$_3$, δ(ppm)):
 1.90 (bs, 1H),
 2.14, 2.22 (2αdd, J = 19, 8.4 Hz, 2H),
 2.02 (s, 3H),
 4.94–5.24 (m, 1H),
 5.75–5.96 (m, 1H),
 6.04, 6.16 (2dm, J = 7 Hz, 2H).
Mass (m/e):
 142 (M+), 126, 125, 100, 99, 82, 43.

It was thus found from the foregoing properties that M-1 was a cis-isomer and M-2 was a trans-isomer.

EXAMPLE 2

Preparation of compound (1-B) by Step 3-B 1.00 gram (10.0 mmols) of 3,5-dihydroxycyclopent-1-ene and 1.19 grams (15.0 mmols) of pyridine were dissolved in 20 milliliters of dioxane in a stream of nitrogen, to which was then added a solution of 0.47 gram (6.0 mmols) of acetic acid chloride in 2.0 milliliters of dioxane, the addition of the latter being made in increments of 100 microliters each at intervals of 1–2 hours at room temperature with stirring. It took a total of 100 hours to complete addition. The aftertreatment was carried out as in Example 1 followed by separation of the reaction mixture to obtain 0.87 gram of an oily substance.

When calculations were made from the results of the gas chromatography (PEG 20 M), the yields of monoacetate and diacetate were 51% and 6%, respectively.

EXAMPLE 3

Preparation of compound (1-B) by Step 3-B

Forty-eight milligrams (0.6 mmol) of acetic acid chloride was added to a mixture of 111 milligrams (1.1 mmols) of 3,5-dihydroxycyclopent-1-ene and 0.5 milliliter of pyridine with stirring over a period of 5 hours. The aftertreatment was carried out as in Example 1, and 62 milligrams of a crude product was obtained. When calculations were made from the results of the chromatographic analysis, the yields of the monoacetate and diacetate were 22% and 7%, respectively.

EXAMPLE 4

Preparation of compound (1-B) by Step 3-B

To a mixture of 1.50 grams (15 mmols) of 3,5-dihydroxycyclopent-1-ene and 1.0 milliliter (120 mmols) of pyridine was added 972 milligrams (9.5 mmols) of acetic anhydride, the addition being made over a period of 7.5 hours with stirring. The aftertreatment was then carried out as in Example 1 to obtain 0.62 gram of a crude product. When calculations were made from the results of the gas chromatographic analysis, the yields of monoacetate and diacetate were 22% and 5%, respectively.

EXAMPLE 5

Preparation of compound (1-B) by Step 3-B

A solution in 2.5 milliliters of anhydrous tetrahydrofuran of 110 milligrams (0.78 mol) of benzoyl chloride immediately after its purification by distillation was added dropwise to a solution of 71 milligrams (0.71 mmol) of 3,5-dihydroxycyclopent-1-ene (a cis:trans = 45:55 mixture) in 79 milligrams (1.0 mmol) of anhydrous pyridine, the addition being made in a stream of nitrogen with stirring, over a period of 13.5 hours at room temperature, using a syringe drive. After concentrating the solvent under reduced pressure with an evaporator, 50 milliliters of ether was added, and the reaction mixture was washed with a saturated sodium bicarbonate solution (5 ml × 2), dilute hydrochloric acid (5 ml × 2) and a saturated sodium chloride solution (5 ml × 2). This was followed by drying the reaction mixture with anhydrous magnesium sulfate and distilling off the solvent under reduced pressure to obtain an oily product. The so obtained product was purified by thin-layer chromatography (developed 10 time with a 95:5 benzene-ether mixture) to obtain 48.6 milligrams and 48.3 milligrams of respectively compounds having Rf = 0.46 and Rf = 0.32. These compounds exhibited the following properties.

The compound of Rf = 0.46

IR (liquid film, cm$^{-1}$):
 3350, 1705.
NMR (CDCl$_3$, δ(ppm) ):
 1.31 (dt, J = 14.5, 4.3 Hz, 1H),
 2.92 (dt, J = 14.5, 7.5 Hz, 1H),
 3.40 (s, 1H),
 4.80 (m, 1H),
 5.75 (m, 1H),
 6.14 (m, 2H),
 7.50, 8.06 (m, 5H).
Mass (m/e):
 204 (M$^+$), 187, 105.

Compound of Rf = 0.32

IR (liquid film, cm$^{-1}$):
 3350, 1710.
NMR (CDCl$_3$, δ(ppm) ):
 2.00 (m, 1H), 2.34 (m, 1H), 2.64 (s, 1H), 5.17 (m, 1H),
 6.13 (m, 1H), 6.18 (s, 2H), 7.50, 8.06 (m, 5H).
Mass (m/e):
 204 (M$^+$), 187, 105.

It was thus found from the foregoing properties that the compound corresponding to Rf = 0.46 was cis-3-benzoyloxy-5-hydroxycyclopent-1-ene (yield 74%) on cis-diol basis) and that the compound corresponding to Rf = 0.32 was trans-3-benzoyloxy-5-hydroxycyclopent-1-ene (yield 61% on trans-diol basis).

EXAMPLE 6

Preparation of compound (2-B) by Step 1-B (1) Preparation of 4-acetoxycyclopent-2-en-1-one 144 milligrams of optically inactive 3-acetoxy-5-hydroxycyclopent-1-ene prepared as in Example 1 and 460 milligrams of 2,3-dichloro-5,6-dicyano-p-benzoquinone (DDQ) were dissolved in 5 milliliters of dioxane, after which the resulting solution was heated with stirring for 48 hours at 60° C. The precipitate separating out after the reaction was separated by filtration, and the filtrate was concentrated under reduced pressure to obtain a crude product.

(2) Separation and Purification

The foregoing crude product was submitted to column chromatography using as solvent a mixture of ethyl acetate and hexane and thereafter to thin-layer chromatography to obtain 100 milligrams of a purified product exhibiting a single spot and having the following properties.

(3) Properties and identification

IR (liquid film, cm$^{-1}$):
 1735, 1710, 1370, 1230, 1180, 1100, 1030, 985, 910, 790.
NMR (60 MHz, CCl$_4$, ppm):
 2.00 (s, 3H),
 2.25 (dd, J = 3Hz, 19Hz, 1H),
 2.75 (dd, J = 6Hz, 10Hz, 1H),
 4.77 (m, 1H),
 6.26 (dd, J = 1Hz, 7Hz, 1H),
 7.25 (dd, J = 2Hz, 7Hz, 1H).
MS (m/e, %):
 140 (M$^+$, 7).
UV (methanol solvent, λmax):
 210 mμ.

The product obtained above was thus identified as being 4-acetoxycyclopent-2-en-1-one from the foregoing properties.

EXAMPLE 7

Preparation of compound (2-B) by Step 1-B (1) Preparation of (R)-trans-3-acetoxy-5-hydroxycyclopent-1-ene to be used as the starting material.

A 5-liter separable round bottom flask was charged with 270 grams of commercial baker's yeast (compressed cake produced by Oriental Yeast Co., Ltd., Japan), 90 grams of glucose, 675 grams of monobasic sodium phosphate and 1.8 liters of deionized water and, after rendering the mixture into a homogeneous solution, it was left to stand for one hour at room temperature. To this solution was then added 18 grams of 3,5-diacetoxycyclopent-1-ene as the substrate, after which the culture was carried out for 48 hours at 32° C. with vigorous stirring using an agitator. After completion of the culture, the culture, the yeast cells were separated from the culture liquid, using a centrifuge. The supernatant liquid, after being salted out with the addition of ammonium sulfate, was extracted with ethyl acetate. The extract obtained by separately extracting the yeast cells with ethyl acetate was combined with the foregoing extract, and the combined extract was dried with Glauber's salt. On distilling off the solvent, 7.35 grams of a crude product was obtained.

The so obtained product was purified by thinlayer chromatography (developing solvent: a mixture of 50 weight parts of ethyl acetate and 50 weight parts of benzene) to obtain 127 milligrams of a liquid of Rf = 0.58, 535 milligrams of a liquid of Rf = 0.25 and 2.58 grams of a liquid of Rf = 0.04. The properties of these liquids were as follows:

Liquid of Rf = 0.25

IR (liquid film, cm$^{-1}$):
3350, 1730, 1430, 1375, 1355, 1250, 1150, 1120.
NMR (60 MHz, CCl$_4$, ppm):
2.00 (s, 3H), 2.10 (m, 2H), 4.35 (s, 1H), 4.90 (m, 1H), 5.75 (m, 1H), 6.00 (m, 2H).
Mass (m/e):
99 (M$^+$ - COCH$_3$), 82, 43.
$[\alpha]_D^{20}$ = +258° (c = 0.032, methanol)

This product was identified as being the (R)-trans-isomer of 3-acetoxy-5-hydroxycyclopent-1-ene from the foregoing properties.

Liquid of Rf = 0.58

IR (liquid film, cm$^{-1}$):
1735, 1240, 1035.
NMR (60 MHz, CCl$_4$, ppm):
2.00 (s, 6H), 2.21 (t, J = 6Hz, 2H), 5.73 (t, J = 6Hz, 2H),
6.06 (s, 2H).
Mass (m/e):
141 (M$^+$ - COCH$_3$), 125, 124, 99, 82, 43.
$[\alpha]_D^{20}$ = +215° (c = 0.023, methanol).

This product was identified as being (R)-trans-3,5-diacetoxycyclopent-1-ene from the foregoing properties.

Liquid of Rf = 0.04

The various spectral data such as IR, Mass and NMR of this product were in agreement with those of a separately synthesized 3,5-dihydroxycyclopent-1-ene, and the cis-isomer to trans-isomer ratio of this product was found to be 17:9 from its gas chromatography. Further, it had a $[\alpha]_D^{20}$ = -15° (c = 0.072, methanol).

(2) Preparation of 4(R)-acetoxycyclopent-2-en-1-one.

A solution of 150 milligrams of the trans-3(R)= acetoxy-5(R)-hydroxycyclopent-1-ene prepared by the method of (1), above, and 480 milligrams of DDQ in 6 milliliters of dioxane was heated with stirring for 48 hours at 60° C. One completion of the reaction, the precipitate separating out was filtrably separated, and the filtrate was concentrated under reduced pressure to obtain a crude product.

The so obtained crude product was then separated and purified as in (2) of Example 6 to obtain 110 milligrams of a purified product. The various spectral data exhibited by this product were in complete agreement with those of the product identified as being 4-acetoxycyclopent-2-en-1-one in (3) of Example 6. Further, as the $[\alpha]_D^{20}$ of this product was +82° (c = 0.063, methanol), it was identified as being 4(R)-acetoxycyclopent-2-en-1-one.

EXAMPLE 8

Preparation of compound (2-B) by Step 1-B (1) Preparation of (S)-trans-3-acetoxy-5-hydroxycyclopent-1-ene to be used as starting material.

A part of the product having a $[\alpha]_D^{20}$ = -15° obtained by the method described in Example 7 was separated into a cis-isomer and a trans-isomer by gas chromatography to obtain (S)-trans-3,5-dihydroxycyclopent-1-ene exhibiting a $[\alpha]_D^{20}$ = -43°. A solution of 0.35 gram of the so obtained product and 0.42 gram of pyridine in 10 milliliters of anhydrous tetrahydrofuran was then reacted with 0.35 gram of acetic acid chloride by operating as in the method of Step 3-B described in Example 1. This was followed by separating and purifying the product as in Example 1 to obtain 230 grams of (S)-trans-3-acetoxy-5-hydroxycyclopent-2-en-1-one having a $[\alpha]_D^{20}$ = -46° and exhibiting IR, NMR and Mass in agreement with the trans-3-acetoxy-5-hydroxycyclopent-1-ene obtained in Example 1.

(2) Preparation of 4(S)-acetoxycyclopent-2-en-1-one.

A solution of 150 milligrams of the (S)-trans-3-acetoxy-5-hydroxycyclonent-1-ene prepared by the method of (1), above, and 480 milligrams of DDQ in 6 milliliters of dioxane was heated with stirring for 48 hours at 60° C. This was followed by separating and purifying the reaction product as in (2) of Example 7 to obtain 115 milligrams of 4(S)-acetoxycyclopent-1-one exhibiting $[\alpha]_D^{20}$ = -17° in complete agreement with the 4-acetoxycyclopent-2-en-1-one identified in (3) of Example 6.

EXAMPLE 9

Preparation of compound (2-B) by Step 1-B 358 milligrams of optically active 3-benzoyloxy-5-hydroxycyclopent-1-ene and 1.3 grams of active manganese dioxide were stirred in a solvent mixture of 2 milliliters of petroleum ether and 3 milliliters of benzene for about 4 hours while being heated under reflux. After completion of the reaction, the precipitate was separated by diltration, and the filtrate was concentrated under reduced pressure to obtain 260 milligrams of a crude product.

On analysis of this product by thin-layer chromatography using silica gel as carrier and a 2:8 hexane-ethyl acetate mixture as the developing solvent, it was found to be a single substance. The yield was 74%. This product exhibited the following properties and was identified as being 4-benzoyloxycyclopent-2-en-1-one.
Melting point: 84° - 85° C. (literature value 85° C.).
UV (methanol solvent, λmax): 228 mμ,
NMR (60 MHz, CCl$_4$, ppm):
2.45 (dd, J = 2Hz, 19Hz, 1H),
2.8 (dd, J = 6Hz, 19Hz, 1H),
6.5 (m, 1H),
6.33 (dd, J = 1Hz, 6Hz, 1H),
7.58 (dd, J = 2Hz, 6Hz, 1H),
7.48 (m, 3H),
7.99 (dd, J = 2Hz, 7Hz, 2H).

EXAMPLE 10

Preparation of compound (2-B) by Step 1-B (1) Preparation of (S)-trans-3-benzoyloxy-5-hydroxycyclopent-1-ene to be used as starting material.

A part of the product exhibiting a $[\alpha]_D^{20} = -15°$ obtained by the method of (1) of Example 7 as analyzed by gas chromatography to separate it into a cis-isomer and a trans- isomer and, as a consequence, (S)-trans-3,5-dihydroxycyclopent-1-ene exhibiting a $[\alpha]_D^{20} = -43°$ was obtained. A solution of 0.069 gram of this substance and 0.070 gram of pyridine in 1.5 milliliters of anhydrous tetrahydrofuran was reacted with 0.12 milliliter of benzoyl chloride by the same method of Step 3-B described in Example 5 followed by separation and purification in same manner as described therein to obtain 0.091 gram of (S)-trans-3-benzoyloxy-5-hydroxycyclopent-1-ene having a $[\alpha]_D^{20} = -49°$ and exhibiting the same IR, NMR and Mass as those of the trans-3-benzoyloxy-5-hydroxycyclopent-1-ene obtained in Example 5.

(2) Preparation of 4(S)-benzoyloxycyclopent-2-en-1-one.

38 milligrams of the (S)-trans-3-benzoyloxy-5-hydroxycyclopent-1-ene obtained by the method of (1), above, was added in 15 milliliters of methylene chloride to a chromic acid-pyridine complex prepared from 100 milligrams of chromic anhydride and 159 milligrams of pyridine, following which the mixture was stirred for 20 minutes at room temperature. The organic layer was then separated, successively washed in a 5% aqueous NaOH solution, 5% aqueous HCl solution and water and dried, after which the solvent was distilled off to obtain 22 milligrams of 4(S)-benzoyloxycyclopent-2-en-1-one having a $\Delta\epsilon_{226} = -14°$ and exhibiting the same IR, NMR and mass as those of the product obtained in Example 9. The yield was 58%.

EXAMPLE 11

Preparation of compound (5) by Step 5

Forty milligrams of Wheat Germ Lipase Type 1 (glycerol-ester hydrolase) EC No. 3.1.1.3 (a product of Sigma Company) and as the substrate 190 milligrams of 4-acetoxycyclopent-2-en-1-one were suspended in 35 milliliters of an acetic acid buffer solution of 0.1 M concentration and pH 5.0, after which the reaction was carried out at 32° C. with vigorous stirring using an agitating propellor.

After a reaction time of 24 hours, further addition of 40 milligrams of the foregoing lipase was made, following which the reaction was carried out for a further 12 hours. After completion of the reaction, the reaction mixture was saturated with ammonium sulfate followed by extraction with ethyl acetate and thereafter drying with magnesium sulfate. The solvent was then distilled off, and 150 milligrams of a product was obtained. On analysis of this product by thin-layer chromatography (developing solvent: a mixture of 50 parts of ethyl acetate and 50 parts of benzene), a single spot was exhibited at Rf = 0.12. The properties of this product were as follows:

IR (liquid film, $cm^{-1}$):
  3350, 1710, 1585, 1400, 1340, 1250, 1100, 1040.
NMR (60 MHz, $CDCl_3$ solvent, ppm):
  2.00–3.10 (m, 2H), 4.33 (s, 1H), 5.10 (m, 1H),
  6.20 (m, 1H), 7,60 (m, 1H)
UV (methanol solvent): $\lambda max = 210$ m$\mu$.

The mass analysis of this product was conducted after silylation of the product with tertiary dimethylsilyl chloride. Thus, the results of the mass analysis of the silylated product of this product were as follows: Mass (70 eV, (m/e): 212 ($M^+$), 197, 155, 81, 75.

The product was thus identified as being 4-hydroxycyclopent-2-en-1-one from the foregoing results.

EXAMPLE 12

Preparation of compound (5) by Step 5

234 milligrams (1.67 mmols) of 4(R)-acetoxycyclopent-2-en-1-one ($[\alpha]_D^{20} = +82°$) and 100 milligrams of the same wheat germ lipase as that used in the method of Example 11 were suspended in 40 milliliters of an acetic acid buffer solution identical to that used in the method of Example 11, after which the treatment was carried out for 48 hours at 32° C. After completion of the reaction, the aftertreatment of the reaction mixture was carried out as in Example 11 to obtain 143 milligrams of a crude product. The physical properties of this product were the same as those obtained by the method of Example 11. The optical activity of this product was $[\alpha]_D^{20} = +59°$ (c = 0.065, methanol). In view of the fact that this product is converted by its acylation with acetic anhydride-pyridine to 4(R)-acetoxycyclopent-2-en-1-one exhibiting an optical rotation to the right, it was identified as being 4(R)-hydroxycyclopent-2-en-1-one.

EXAMPLE 13

Preparation of compound (5) by Step 5

Rinds of tangerine were crushed with a mixer and then extracted with a 0.2% aqueous sodium chloride solution, following which the ring residue was separated and removed with a centrifuge. The supernatant liquid of the extract was then saturated with ammonium sulfate to precipitate the protein fraction, which was then collected by centrifugation. This protein fraction was dialyzed against deionized water, and the resulting enzyme solution was used as the crude citrus esterase solution.

Twenty milligrams of this enzyme solution and as the substrate 50 milligrams of 4-acetoxycyclopent-2-en-1-one were suspended in 10 milliliters of a sodium phosphate buffer solution of 0.05 M concentration and pH 7.0, following which the reaction was carried out at 32° C. with vigorous stirring using an agitating propellor. After about 40 hours, the reaction mixture was analyzed by thin-layer chromatography. As a spot of the starting 4-acetoxycyclopent-2-en-1-one was noted, a further addition of 20 milligrams of the enzyme solution was made, after which the reaction was carried out in like manner for about 9 hours more. Thereafter, the experiment was operated as in Example 11 to obtain 31 milligrams of a crude product, which was separated and purified by thin-layer chromatography (4:6 ethyl acetate/n-hexane mixture) to obtain 22 milligrams of liquid of Rf = 0.14. The various spectral data were in agreement with those of 4-hydroxycyclopent-2-en-1-one.

EXAMPLE 14

Preparation of compound (4-A) by Step 4

Nineteen milligrams (0.134 mmol) of 3-acetoxy-5-hydroxycyclopent-1-ene was dissolved in 0.5 milliliters of anhydrous dimethylformamide, to which were then added 24 milligrams (0.16 mmol) of t-butyldimethylsilyl chloride and 23 milligrams (0.34 mmol) of imidazole, after which the mixture was reacted for 24 hours at room temperature under a nitrogen atmosphere with stirring. Five milliliters of water was added to the reaction mixture, which was then extracted with hexane. Next, the resulting organic layer was thoroughly washed in water, dried with anhydrous sodium sulfate and thereafter concentrated to obtain 33 milligrams of a crude product. When this product was analyzed by thin-layer chromatography (silica gel 0.25 mm, hexane:ethyl acetate = 1:1), a spot was only noted at Rf = 0.70, and since it gave the following spectral data, it was identified as being 3-butyldimethylsilyloxy-5-acetoxycyclopent-1-ene. 33 milligrams correspond to 129 mmols, and the yield was 96%.

IR (liquid film, cm$^{-1}$):
   3020, 1730, 1240, 1125, 1070, 1020, 900, 835, 775.
NMR (60 MHz, CCl$_4$, δ(ppm) ):
   0.05 (6H, singlet),
   0.88 (9H, singlet),
   1.94 (3H, singlet),
   Vicinity of 2.0 (2H, multiplet),
   5.0 (1H, multiplet),
   5.65 (1H, multiplet),
   5.65 (1H, multiplet),
   5.90 (2H, singlet),
Mass (70 eV, m/e):
   256 (M$^+$).

EXAMPLE 15

Preparation of compound (4-A) by Step 4

By operating as in Example 14, 590 milligrams (4.15 mmols) of optically active 3-acetoxy-5-hydroxycyclopent-1-ene[[α]$_D^{20}$ = +162° (c = 0.103, CH$_3$OH) ] was dissolved in 2 milliliters of anhydrous dimethylformamide, to which solution were added 1.0 gram (6.7 mmols) of t-butyldimethylsilyl chloride and 1.0 gram (14.7 mmols) of imidazole. The mixture was then reacted for 64 hours at room temperature in an atmosphere of nitrogen with stirring. After completion of the reaction, 20 milliliters of water was added to the reaction mixture, following which the reaction mixture was extracted with hexane. The resulting organic layer was thoroughly washed in water, dried with anhydrous sodium sulfate and thereafter concentrated to obtain 1.34 grams of a crude product. This product was then separated and purified by column chromatography (silica gel). First, the product was eluted with 200 milliliters of hexane, after which it was eluted with a developing solution consisting of a 2:1 hexane-ethyl acetate mixture. On concentration of this eluate, 1.06 grams of a product was obtained having a spot at Rf = 0.60 when analyzed by thin-layer chromatography (silica gel 0.25 mm, hexane:ethyl acetate = 2:1) and a single peak when analyzed by gas chromatography (PEG 20M, 20%, 2 mm × 3 mm diameter, 180° C.). Since this product exhibited the following spectral data, it was identified as being 3-t-butyldimethylsiloxy-5-acetoxycyclopent-1-ene. 1.06 grams correspond to 4.10 mmols, and the yield was 99%.

IR (liquid film, cm$^{-1}$):
   3020, 1730, 1260 - 30, 1125, 1070, 1030, 900, 835, 775.
NMR (60 MHz, CCl$_4$, δ(ppm):
   0.05 (6H, singlet),
   0.88 (9H, singlet),
   1.94 (3H, multiplet),
   Vicinity of 2.0 (2H, multiplet),
   5.0 (1H, multplet),
   5.90 (2H, singlet).
Mass (70 eV, m/e):
   256 (M$^+$),
   [α]$_D^{20}$ = +89° (c = 0.059, CH$_3$OH).

EXAMPLE 16

Preparation of compound (4-A) by Step 4

By operating as in Example 15, 557 milligrams (3.93 mmols) of optically active 3-acetoxy-5-hydroxycyclopent-1-ene [ [α]$_D^{20}$ = +162° (c = 0.103, CH$_3$OH) ] was dissolved in 5 milliliters of anhydrous dimethylformamide, to which solution were then added 2.5 grams (16.7 mmols) of t-butylsilyl chloride and 2.0 grams (29.4 mmols) of imidazole, after which the reaction was carried out for 48 hours at room temperature in an atmosphere of nitrogen with stirring. This was followed by adding 30 milliliters of water to the reaction mixture and extraction of the mixture with ether. The resulting organic layer was then throughly washed in water, dried with anhydrous sodium sulfate and thereafter concentrated to obtain 2.74 grams of a crude product. The so obtained product was separated and purified by column chromatography as in Example 15 to obtain 980 milligrams (3.83 mmols, 97%) of 3-t-butyldimethylsiloxy-5-acetoxycyclopent-1-ene.

EXAMPLE 17

Preparation of compound (4-A) by Step 4

By operating as in Example 15, 120 milligrams (0.85 mmol) of optically active 3-acetoxy-5-hydroxycyclopent-1-ene [ [α]$_D^{20}$ = +160° (CH$_3$OH) ] was dissolved in 0.5 milliliters of anhydrous dimethylformamide and, after adding 153.5 milligrams (1.02 mmols) of t-butyldimethylsilyl chloride and 144.5 milligrams (2.13 mmols) of imidazole thereto, the reaction was carried out by allowing the mixture to stand for 72 hours at room temperature in an atmosphere of nitrogen. After adding 5 milliliters of water to the reaction mixture, it was extracted with hexane, following which the resulting organic layer was washed thoroughly in water, dried with anhydrous sodium sulfate and thereafter concentrated to obtain 212 milligrams of the intended product. As a result of analyses of this product by thin-layer chromatography and gas chromatography, it was found to be a single substance, and from its spectral data it was identified as being 3-t-butyldimethylsiloxy-5-acetoxy-cyclopent-1-ene.

212 milligrams correspond to 0.83 millimol, and the yield was 98%.

EXAMPLE 18

Preparation of compound (4-A) by Step 4

By operating as in Example 15, 440 milligrams (3.1 mmols) of optically active 3-acetoxy-5-hydroxycyclopent-1-ene [ [α]$_D^{20}$ = +7.7° (CH$_3$OH) ] was dissolved in 1.8 milliliters of anhydrous dimethylformamide and, after adding 557 milligrams (3.1 mmols) of t-butyldimethylsilyl chloride and 530 milligrams (7.8 mmols) of imidazole thereto, the reaction was carried out by allowing the mixture to stand for 24 hours at room temperature in an atmosphere of nitrogen. This was followed by adding 10 milliliters of water to the reaction mixture and extraction of the mixture with hexane. The resulting organic layer was then washed thoroughly in water, dried with anhydrous mangnesium sulfate and thereafter concentrated to obtain 630 milligrams of the product. As a result of analyses of this product by thin-layer chromatography and gas chromatography, it was found to be a single substance, and from its spectral data it was identified as being 3-t-butyldimethylsiloxy-5-acetoxy-cyclopent-1-ene. 630 milligrams correspond to 2.46 millimols, and the yield was 79%. The specific rotation of this compound was +6.3° ($CH_3OH$).

EXAMPLE 19

Preparation of compound (4-A) by Step 4

One hundred milligrams (0.49 mmols) of 3-hydroxy-5-benzoyloxycyclopent-1-ene was dissolved in 0.5 milliliters of anhydrous dimethylformamide and, after adding 9.0 milligrams (0.60 mmol) of t-butyldimethylsilyl chloride and 85 milligrams (1.25 mmols) of imidazole thereto, the reaction was carried out for 48 hours at room temperature in an atmosphere of nitrogen with stirring. This was followed by adding 5 milliliters of water to the reaction mixture and extracting the reaction mixture with hexane. The resulting organic layer was then thoroughly washed in water, dried with anhydrous sodium sulfate and thereafter concentrated to obtain a crude product. This crude produce was separated by preparative thin-layer chromatography (silica gel, hexane:ethyl acetate = 2:1), and 140 milligrams (0.44 mmol, 90%) of the intended product was obtained. Since this product exhibited the following spectral data, it was identified as being 3-t-butyldimethylsiloxy-5-benzoyloxycyclopent-1-ene.

IR (liquid film, $cm^{-1}$):
  3020, 1710, 1603, 1585, 1450, 1265, 1110, 1070, 1030,
  900, 835, 795, 775, 715.
NMR (60 MHz, $CCl_4$, δ(ppm):
  0.05 (6H, singlet),
  0.88 (9H, singlet),
  Vicinity of 2.0 (multiplet),
  5.0 (1H, multiplet),
  5.7–5.8 (1H, multiplet),
  6.10 (2H, singlet),
  7.36, 7.90 (3H and 2H, multiplet).
Mass (70 eV, m/e):
  318 ($M^+$).

EXAMPLE 20

Preparation of compound (4-A) by Step 4

150 milligrams (0.47 mmol) of 3-(+)-alphamethoxy-alpha-trifluoromethylphenylacetoxy-5-hydroxycyclopent-1-ene was dissolved in 0.5 milliliters of anhydrous dimethylformamide, after which 90 milligrams (0.60 mmol) of t-butyldimethylsilyl chloride and 90 milligrams (1.32 mmols) of imidazole were added thereto. The resulting solution was then reacted for 48 hours at room temperature in an atmosphere of nitrogen with stirring. After completion of the reaction, 5 milliliters of water was added to the reaction mixture, which was then extracted with hexane. The resulting organic layer was thoroughly washed in water, dried with anhydrous sodium sulfate and thereafter concentrated to obtain a crude product. This crude product was separated by preparative thin-layer chromatography (silica gel, hexane:ethyl acetate = 2:1), and 185 milligrams (0.43 mmol, 9.1%) of the intended product was obtained. Since this product provided the following spectral data, it was identified as being 3-t-butyldimethylsiloxy-5-(+)-alpha-methoxyalpha-trifluoromethylphenylacetoxycyclopent-1-ene.

IR (liquid film, $cm^{-1}$):
  3020, 1740, 1600, 1260, 1170, 1120, 1070, 1020, 900,
  840, 770, 710, 690.
NMR (60 MHz, $CCl_4$, δ(ppm):
  0.05 (6H, singlet),
  0.86 (9H, singlet),
  2.1–2.2 (2H, multiplet),
  3.50 (3H, singlet),
  5.0 (1H, multiplet),
  5.9 (1H, multiplet),
  6.01 (2H, multiplet),
  7.38 (5H, multiplet).
Mass (70 eV, m/e):
  430 ($M^+$).

EXAMPLE 21

Preparation of compound (4-A) by Step 4

Forty-three milligrams of (S)-trans-3-acetoxy-5-hydroxycyclopent-1-ene ($[\alpha]_D^{20}$ = −46°) obtained in (1) of Example 8 was dissolved in 0.5 milliliter of dimethylformamide and, after adding 56 milligrams of t-butyldimethylsilyl chloride and 54 milligrams of imidazole thereto, the reaction was carried out for 24 hours at room temperature with stirring. Ten milliliters of water was then added to the reaction mixture, after which the mixture was extracted with hexane. The resulting organic layer was then washed thoroughly in water and thereafter dried to obtain 61 milligrams of the intended product. As a result of thin-layer chromatography and spectral data thereof, this product was identified as being 3-t-butyldimethylsiloxy-5-acetoxycyclopent-1-ene [$[\alpha]_D^{20}$ = −43° (methanol)]. The yield was 77%.

EXAMPLE 22

Preparation of compound (4-A) by Step 4

142 milligrams of 3-acetoxy-5-hydroxycyclopent-1-ene obtained in Example 1 was dissolved in 5 milliliters of methylene chloride, to which were then added 0.5 milliliter of dihydropyran and a catalytic amount of p-toluenesulfonic acid, following which the reaction was carried out for 24 hours at room temperature with sitrring. After completion of the reaction, the reaction product was washed in a 5% aqueous sodium bicarbonate solution followed by water-washing, drying and removal of the solvent and excess dihydropyran under reduced pressure to obtain 192 milligrams of a crude product (yield 85%). On analysis of this product by thin-layer chromatography (cyclohexane:ethyl acetate = 8:2), a single spot (Rf = 0.70) was observed, and the following properties were exhibited.

IR (liquid film, $cm^{-1}$):
  1720, 1130, 1020.
NMR ($CCl_4$, δ(ppm)):
  1.57 (bs, 8H), 2.05 (s, 3H), 3.8 (m, 2H), 4.8 (m, 3H),
  5.9 (s, 2H).
Mass (m/e):
  226 ($M^+$).

This product was found to be 3-acetoxy-5-tetrahydropyranyloxycyclopent-1-ene from the foregoing properties.

EXAMPLE 23

Preparation of compound 4-A by Step 4

(1) Preparation of 4-alpha-methoxy-alpha-trifluoromethyl-alpha-phenylacetoxy cyclopent-2-en-1-ol to be used as starting material.

Thirty-five milligrams of cyclopent-2-en-1,4-diol was dissolved in 2 milliliters of carbon tetrachloride and, after adding 0.7 milliliter of alpha-methoxy-alpha-trifluoromethyl-alpha-phenylacetic acid chloride thereto, 6 drops of pyridine were added dropwise thereto. The mixture was then stirred for 12 hours at room temperature, after which 10 milliliters of ether was added. The resulting organic layer was washed in a 5% sodium bicarbonate solution, 5% hydrochloric acid and water, in the order given, followed by drying with anhydrous magnesium sulfate and thereafter distilling off the organic solvent under reduced pressure to obtain an oily product. When the so obtained product was purified by thin-layer chromatography (n-hexane: ethyl acetate = 4:6), 66 milligrams (60%) of 4-alpha-methoxy-alpha-trifluoromethyl-alpha-phenylacetoxycyclopent-2-en-1-ol was obtained.

IR (liquid film, cm$^{-1}$):
  3300, 1735.
NMR (CDCl$_3$, δ(ppm)):
  7.45 (5H), 3.51 (3H), 5.85 (2H), 4.88 (2H), 1.90 (2H), 2.2 (1H)

(2) Preparation of 1-t-butyldimethylsiloxy-4-alpha-methoxy-alpha-trifluoromethyl-alpha-phenylacetoxy-cyclopent-2-ene.

Sixty-six milligrams of 4-alph-methoxy-alpha-trifuluoromethyl-alpha-phenylacetoxycyclopent-2-en-1-ol was dissolved in 1.0 milliliter of dimethylformamide, after which 38 milligrams of t-butyldimethylsilyl chloride and 36 milligrams of imidazole were added thereto followed by stirring the mixture for 24 hours at room temperature. Ten milliliters of water was then added to the reaction mixture, after which the mixtuee was extracted with hexane. The resulting organic solution was thoroughly washed with water followed by drying with anhydrous magnesium sulfate and distilling off the solvent under reduced pressure to obtain 73 milligrams (81%) of the intended product.

IR (liquid film, cm$^{-1}$):
  1735.
NMR (CDCl$_3$, δ(ppm)):
  0.1 (6H), 0.9 (9H), 7.45 (5H), 3.50 (3H), 5.90 (3H), 4.90 (2H), 1.90 (2H).

EXAMPLE 24

Preparation of compound (4-A) by Step 4

Seventy-one milligrams of 3-acetoxy-5-hydroxycyclopent-1-ene obtained in Example 1 was suspended in 5 milliliters of tetrahydrofuran, to which was then added 12 milligrams of sodium hydride. Next, after adding 86 milligrams of benzyl bromide, the mixture was stirred for 3 hours at room temperature. Thirty milliliters of water was then added to the reaction mixture followed by its extraction with ether. The resulting organic layer was then washed in water and dried with anhydrous magnesium sulfate, after which the solvent was distilled off under reduced pressure to obtain 105 milligrams (yield 89%) of the itended product. On analysis of this product by thin-layer chromatograph, it exhibited a single spot (Rf = 0.65), and its spectral data were as follows:

IR (liquid film, cm$^{-1}$):
  3050, 1720, 1230, 1100, 735, 690.
NMR (CCl$_4$, δ(ppm)):
  1.94 (s, 3H), 2.0 (m, 2H), 4.30 (s, 2H), 5.0 (m, 1H), 5.7 (m, 1H), 5.90 (s, 2H), 7.21 (s, 5H)
Mass (m/e):
  232 (M$^+$).

It was thus found from the foregoing properties that the product was 3-acetoxy-5-benzyloxycyclopent-1-ene.

EXAMPLE 25

(4-A) $\xrightarrow{\text{Step 2-A-1}}$ (1-A)

Thirty-three milligrams (0.129 mmol) of 3-acetoxy-5-t-butyldimethylsiloxycyclopent-1-ene was dissolved in 2 milliliters of anhydrous diethyl ether and, after adding 20 milligrams (0.53 mmol) of lithium aluminum hydride thereto, the reaction was carried out for 16 hours at room temperature in an atomosphere of nitrogen with stirring. After completion of the reaction, a saturated aqueous solution of sodium sulfate was slowly added dropwise to the reaction mixture to hydrolyze the excess lithium a aluminum hydride. The resulting solid was then separated by filtration and wahsed in ether. It was then combined with the filtrate, dried with sodium sulfate and thereafter concentrated to obtain 23 milligrams of a crude product. On analysis of this product by thin-layer chromatography, only a spot at Rf = 0.50 was noted. Again, it gave a single peak when analyzed by gas chromatography (PEG 20 M, 20%, 2 m × 3mm diameter 180°). Further, it provided the following spectral data. Hence, this product was identified as being 3-t-butyldimethylsiloxy-5-hydroxycyclopent-1-ene. 23 milligrams correspond to 0.107 millimols, and the yield was 83%.

IR (liquid film, cm$^{-1}$):
  3300, 3020, 1250, 1120, 1080–1060, 900, 835, 775.
NMR (60 MHz, CCl$_4$, δ(ppm)):
  0.05 (6H, singlet),
  0.88 (9H, singlet),
  1.92 (2H, triplet),
  3.60 (1H, singlet),
  Vicinity of 4.9 (2H, multiplet),
  5.84 (2H, singlet).
Mass (11 eV, m/e):
  214 (M$^+$).

EXAMPLE 26

(4-A) $\xrightarrow{\text{Step 2-A-1}}$ (1-A)

970 milligrams (3.97 mmols) of optically active 3-acetoxy-5-t-butyldimethylsiloxycyclopent-1-ene [α]$_D^{20}$ = +89° (c = 0.059, CH$_3$OH) was held in 15 milliliters of anhydrous diethyl ether along with 160 milligrams (4.2 mmols) of lithium aluminum hydride under an atmosphere of nitrogen for 30 minutes at 0° C. and then for 2 hours at room temperature, after which the mixture was heated under reflux for 30 minutes. This was followed by submitting the reaction mixture to an aftertreatment with a saturated aqueous solution of sodium sulfate as in Example 25 to obtain 780 milligrams of a crude product. This product was deemed to consist of a single component from both its thin-layer chromatography and gas chromatography, and it was confirmed to be 3-t-butylmethylsiloxy-5-hydroxycyclopent-1-ene from the following spectral data. 780 milligrams correspond to 3.64 millimols, and the yield was 96%.

IR (liquid film, cm$^{-1}$):

3300, 3020, 1250, 1120, 1080–1060, 900, 835, 775.
NMR (100 MHz, CCl$_4$, δ(ppm)):
 0.05 (6H, singlet),
 0.88 (9H, singlet),
 1.92 (2H, triplet),
 3.60 (1H, singlet),
 Vicinity of 4.9 (2H), multiplet,
 5.84 (2H, singlet),
Mass (11 eV, m/e):
 214 (M$^+$)
Optical rotation: $[\alpha]_D^{20} = +67°$ (c = 0.057, CH$_3$OH).

EXAMPLE 27

(4-A) $\xrightarrow{Step\ 2\text{-}A\text{-}1}$ (1-A)

By operating as in Example 25, 140 milligrams (0.44 mmol) of 3-benzoyloxy-5-t-butyldimethylsiloxycyclopent-1-ene was held in anhydrous ether with 30 milligrams (0.79 mmol) of lithium aluminum hydride for one hour at room temperature under a nitrogen atmosphere, following which the mixture was heated under reflux for 30 minutes. Thereafter the aftertreatment was carried out as in Example 25, and the resulting crude product was separated by preparative thin-layer chromatograph (silica gel 2mm, hexane:ethyl acetate = 4:1) to obtain 85 milligrams (0.04 mmol, 91%) of 3-t-butyldimethylsiloxy-5-hydroxycyclopent-1-ene.

EXAMPLE 28

(4-A) $\xrightarrow{Step\ 2\text{-}A\text{-}1}$ (1-A)

Two hundred milligrams (0.78 mmol) of 3-acetoxy-5-t-butyldimethylsiloxycyclopent-1-ene was dissolved in 1.0 milliliter of a methanol solution of 1 normal barium hydroxide, after which the resulting solution was heated under reflux for 15 minutes in an atmosphere of nitrogen. The methanol was then distilled off under reduced pressure, after which ethanol was added to precipitate a solid, which was filtered off. Ehtanol was then distilled off from the filtrate, after which the concentrated residue was extracted with ether after addition of water thereto. The resulting organic layer was then thoroughly washed in water, dried with anhydrous sodium sulfate and thereafter concentrated to obtain a crude product. The so obtained product was then separated by preparative thin-layer chromatography (silica gel 2mm, hexane:ethyl acetate = 4:1) to obtain 75 milligrams (0.35 mmol, 45%) of 3-t-butyldimethylsiloxy-5-hydroxycyclopent-1-ene.

EXAMPLE 29

(4-A) $\xrightarrow{Step\ 2\text{-}A\text{-}1}$ (1-A)

By operating as in Example 25, 185 milligrams (0.43 mmol) of 3-t-butyldimethylsiloxy-5-(+)-alpha-methoxy-alpha-trifluoromethylphenylacetoxycyclopent-1-ene was held at room temperature for 2 hours in anhydrous diethyl ether with 38 milligrams (1.00 mmol) of lithium aluminum hydride in an atmosphere of nitrogen and thereafter heated under reflux for one hour. Thereafter the aftertreatment was carried out as in Example 25, and the resulting crude product was separated by preparative thin-layer chromatography (silica gel 2mm, hexane:ethyl acetate = 4:1) to obtain 75 milligrams (0.35 mmol, 81%) of 3-t-butyldimethylsiloxy-5-hydroxycyclopent-1-ene.

EXAMPLE 30

(4-A) $\xrightarrow{Step\ 2\text{-}A\text{-}2}$ (1-A)

Rinds of tangerine were crushed with a mixer and then extracted with a 0.2% aqueous sodium chloride solution, following which the rind residue was separated and removed with a centrifuge. The supernatant liquid of the extract was then saturated with ammonium sulfate to precipitate the protein fraction, which was then collected by centrifugation. This protein fraction was dialyzed against deionized water, and the resulting enzyme solution was used as the crude citrus esterase solution. Three milliliters of this enzyme solution and as the substrate 69 milligrams of 3-acetoxy-5-t-butyl-dimethyl-siloxycyclopent were suspended in 3.0 milliliters of a potassium phosphate buffer solution of 0.1 M concentration and pH 7.0 and subjected to an ultrasonic treatment at 32° C. for 15 minutes. A further addition of 2.0 milliliters of the foregoing enzyme solution was then made, after which the reaction was carried out for 48 hours at 32° C. with vigorous stirring using an agitating propeller. After completion of the reaction, the reaction mixture was extracted with ethyl acetate and dried with magnesium sulfate. When the solvent was distilled off, 43 milligrams of the intended product was obtained. On analysis of this product by gas chromatography (PEG 6000, 180° C.), it exhibited a small peak (20%) at a holding time of 10 minutes and 30 seconds (substrate 3-acetoxy-5-t-butyldimethylsiloxycyclopentene) and a large peak (80%) at 14 minutes and 40 seconds (3-t-butyldimethylsiloxy-5-hydroxycyclopentene). When this product was purified and collected by preparative thin-layer chromatography, 30 milligrams of 3-t-butyl-cimethylsiloxy-5-hydrocyclopentene was obtained. That is, as the properties of this product was in complete agreement with those of the product of Example 25, it was identified as being 3-t-butyldimethylsiloxycyclopentene.

EXAMPLE 31

One milliliter of the enzyme solution used in Example 30 and as the substrate 20 milligrams of 3-acetoxy-5-butyldimethylsiloxycyclopentene were suspended in 1.0 milliliter of a potassium phosphate buffer solution of 0.1 M concentration and pH 7.0, and the reaction was carried out at 32° C. with vigorous stirring using an agitating propellor. After a reaction time of 24 hours, a further addition of 1.0 milliliter of the enzyme solution was made, following which the reaction was carried out for a further 24 hours. After completion of the reaction, the reaction mixture was extracted with ethyl acetate and dried with magnesium sulfate. The solvent was then distilled off to obtain 12 milligrams of the intended product. When this product was analyzed by gas chromatography (PEG 6000, 180° C.), it exhibited peaks at a holding time of 10 minutes and 30 seconds (substrate 3-acetoxy-5-t-butyldimethylsiloxycyclopentene, 40%) and 14 minutes and 40 seconds (3-t-butyldimethylsiloxy-5-hydroxycyclopentene, 60%). Further, when this product was analyzed by thin-layer chromatography (developing solvent: a mixture of 50 parts of ethyl acetate and 50 parts of benzene), there was exhibited a spot at Rf = 0.63 corresponding to the substrate, as well as a new spot at Rf = 0.43 (3-t-butyldimethylsiloxy-5-hydroxycyclopentene) resulting from the reaction. On treatment of the so obtained product as in Example 30, 6 milligrams of 3-t-butyldimethylsiloxy-5-hydroxycyclopentene was obtained.

EXAMPLE 32

(3) Step 3-A (1-A)

One gram of 2-cyclopentene-1,4-diol and 1.70 grams of imidazole were dissolved in 4 milliliters of dimethylformamide, to which was then added 1.65 grams of t-butyldimethylsilyl chloride at once, after which the mixture was allowed to stand at room temperature (25° C.) with stirring. The reaction mixture was then introduced into water and, after addition of ether, the organic layer was separated, following which the water later was extracted three times with ether. The ether layer was then washed with saturated brine and dried with anhydrous magnesium sulfate, after which the ether was distilled off under reduced pressure to obtain 1.86 grams of a crude product. When this product was vacuum distilled, fractions shown in Table 1 were obtained, the compositions of which were determined by gas chromatography. Pure monosilyl ether and disilyl ether were purified and collected by thin-layer chromatography.

Table 1

| Fraction (mg) | Boiling Point (° C./0.06 mmHg) | Product Monoether (%) | Diether (%) |
|---|---|---|---|
| 280 | 73 – 74 | 74 | 26 |
| 350 | 74 – 75 | 74 | 26 |
| 210 | 75 – 76 | 66 | 34 |
| 630 | 76 | 24 | 76 |

The properties of the resulting-4-t-butyldimethylsiloxycyclopent-2-en-1-ol were as follows:

IR (liquid film, cm$^{-1}$):
  3050, 3000, 2900, 1460, 1360, 1250, 1120, 1060, 900, 830, 770.

NMR (60 MHz, CCl$_4$, δ(ppm)):
  0.00 (s, 6H), 0.80 (s, 9H), 1.36 (dt, J = 6Hz, 15Hz), 2.60 (dt, J = 7Hz, 15 Hz), 1.84 (t, J = 7Hz, 2H), 4.40 (m, 1H), 4.86 (m, 1H), 5.68 (s, 2H), 2.73 (bs, 1H).

Mass (m/e, %):
  214 (M$^+$, 16).

On the other hand, the 1,4-di(t-butyldimethylsiloxy)-cyclopent-2-ene exhibited the following properties.

IR (liquid film, cm$^{-1}$):
  3050, 2930, 2840, 1460, 1365, 1250, 1130, 1080, 900, 835.

NMR (60 MHz, CCl$_4$, δ(ppm)):
  0.00 (s, 12H), 0.80 (s, 18H), 1.40 (dt, J = λHz, 18Hz), 2.57 (dt, J = 7Hz, 15 Hz), 1.87 (t, J = 6Hz, 2H), 4.46 (t, J = 7Hz) and 4.87 (t, J = 7Hz, 2H), 5.64 (d, J = 3Hz, 2H).

Mass (m/e, %):
  328 (M$^+$, 3).

EXAMPLE 33

(3) Step 3-A (1-a)

2.70 grams of 2-cyclopentene-1,4-diol and 4.61 grams of imidazole were dissolved in 14 milliliters of dimethylformamide, after which 4.50 grams of t-butyldimethylsilyl chloride divided into five portions was added thereto gradually over a period of 12 hours. The reaction mixture was then left to stand overnight at room temperature, following which it was treated as in Example 33 to obtain 5.33 grams of a crude product. It was found on analysis by gas chromatography that this product contained 43% of monosilyl ether and 57% of disilyl ether.

EXAMPLE 34

(3) Step 3-A (1-A)

2.80 grams of cyclopentene-1,4-diol and 4.61 grams of imidazole were dissolved in 30 milliliters of dimethylformamide, to which was then added dropwise over a period of about 4 hours a solution of 4.50 grams of t-butyldimethylsilyl chloride in 15 milliliters of dimethylformamide. The reaction mixture was then left to stand overnight at room temperature and thereafter treated as in Example 33 to obtain 4.53 grams of a crude product. It was found on analysis by gas chromatography that this product contained 35% of monosilyl ether and 65% of disilyl ether.

EXAMPLE 35

(3) Step 3-A (1-A)

210 milligrams of optically active 2-cyclopentene-trans-1,4-diol ($[\alpha]_D^{20} = -81°$) and 260 milligrams of imidazole were dissolved in 0.8 milliliters of dimethylformamide. To this solution was then added at room temperature 240 milligrams of t-butyldimethylsilyl chloride divided into five portions over a period of about 5 hours at intervals of about one hours. The after-treatment of the reaction mixture was then carried out as in Example 33 to obtain 216 milligrams of a crude product. It was found on analysis by gas chromatography that this product contained 60% of monosilyl ether and 40% of disilyl ether. When the crude product was separated by thin-layer chromatography, 105 milligrams of monosilyl ether ($[\alpha]_D^{20} = -38°$) and 67 milligrams of disilyl ether ($[\alpha]_D^{20} = -73°$) were obtained.

EXAMPLE 36

(3) Step 3-A (1-A)

Ten milligrams of (R)-trans-3,5-dihydroxycyclopent-1-ene and 8 milligrams of dihydropyran were stirred at room temperature for 24 hours in 1.0 milliliter of methylene chloride in the presence of 0.1 milligram of p-toluenesulfonic acid. The organic solution was first washed with an aqueous sodium bicarbonate solution and then with an aqueous sodium chloride solution followed by drying with magnesium sulfate and thereafter distilling off the solvent under reduced pressure to obtain a crude product. This product was purified by thin-layer chromatography (n-hexane:ethyl acetate = 6:4), and 11 milligrams (60%) of (R)-trans-5-tetrahydropyranyloxycyclopent-1-en-3-ol was obtained.

IR (liquid film, cm$^{-1}$):
  3300.

NMR (CDCl$_3$, δ(ppm)):
  1.60 (6H), 1.85 (2H), 2.70 (1H), 3.65 (2H), 4.80 (3H), 5.70 (2H).

EXAMPLE 37

(3) Step 3-A (1-A)

Ten milligrams of (S)-trans-3,5-dihydroxycyclopent-1-ene and 8 milligrams of dihydropyran were stirred at room temperature for 24 hours in 1.0 milliliter of methylene chloride in the presence of 0.1 milligram of p-toluenesulfonic acid. Next, the organic solution was washed with an aqueous sodium bicarbonate solution and then with an aqueous sodium chloride solution, after which it was dried with anhydrous magnesium sulfate followed by distilling off the solvent under reduced pressure. When the resulting crude product was purified by thin-layer chromatography (n-hexane:ethyl acetate = 6:4), 10 milligrams (54%) of (S)-trans-5-tetrahydropyranyloxycyclopent-1-en-3-ol was obtained. The IR and NMR of this product was in complete agreement with those of the product obtained in Example 36.

EXAMPLE 38

(4-B) $\xrightarrow{\text{Step 2-B}}$ (1-B)

Forty-two milligrams (0.23 mmol) of trans-cyclopentene-3(R), 5(R)-dioldiacetate ($[\alpha]_D^{25}$ = +208°, in methanol), 16.6 milligrams (0.23 mmol) of n-butylamine and 1.0 milliliter of methyl alcohol were stirred at room temperature for 21 hours. After distilling off the solvent under reduced pressure, 50 milliliters of ether was added to the mixture, following which the organic layer was washed with dilute hydrochloric acid and a saturated aqueous sodium chloride solution and dried with anhydrous magnesium sulfate. The solvent was then distilled off to obtain an oily product. This product was separated by thin-layer chromatography to obtain 25 milligrams (79% yield) of trans-cyclopentene-3(R), 5(R)-diolmonoacetate ($[\alpha]_D^{25}$ = +230°, methanol). The properties of this product were as follows:

IR (coated, cm$^{-1}$):
  33350, 1720.
NMR (CDCl$_3$, δ(ppm)):
  1.90 (s, 1H), 2.02 (s, 3H), 2.18 (m, 2H), 5.08 (m, 1H), 5.84 (m, 1H), 6.10 (m, 2H).

EXAMPLE 39

(4-B) $\xrightarrow{\text{Step 2-B}}$ (1-B)

One gram (5.4 mmols) of trans-cyclopentene-3(R), 5(R)-dioldiacetate ($[\alpha]_D^{25}$ = +208°, in methanol) and 330 milligrams (2.7 mmols) of L-(−)-1-phenylethylamine were stirred in 15 milliliters of methanol for 45 hours at room temperature. After distilling the excess methanol off under reduced pressure, 50 milliliters of ethyl acetate was added to the mixture, which was then washed with dilute hydrochloric acid and a saturated aqueous sodium chloride solution. The organic layer was then dried with anhydrous magnesium sulfate, and the solvent was distilled off to obtain an oily product. This product was purified by thin-layer chromatography (ether, Rf = 0.36) to recover 0.40 gram (40%) of the starting diacetate and obtain 0.345 gram (45% yield) of a monoacetate.

EXAMPLE 40

(1-A) $\xrightarrow{\text{Step 1-A}}$ (2-A)

(1) Preparation of 4-t-butyldimethylsiloxycyclopent-2-en-1-one 1.13 grams of 2,3-dichloro-5,6-dicyano-p-benzoquinone (DDQ) was dissolved in 15 milliliters of dioxane, to which was then added 660 milligrams of crude 4-t-butyldimethylsiloxycyclopent-2-en-1-ol (purity 74%), after which the mixture was heated at 55° C. for 16 hours with stirring. After completion of the reaction, the precipitate separating out was filtered off. When the filtrate was concentrated under reduced pressure, 2.0 grams of a crude product was obtained.

(2) Separation and Purification

The foregoing crude product was passed through a silica gel (20 grams) column, and the fraction (5 × 35 ml) eluted with the use of a hexane-ethyl acetate solvent mixture (weight ratio of mixture 2:3) was collected, after which the solvent was distilled off under reduced pressure to obtain 0.70 grams of the intended product. When this product was developed by thin-layer chromatography using the same solvent mixture as that used above, 336 milligrams (yield 70%) of a purified product exhibiting the following properties were obtained.

(3) Properties and Identification (IR (liquid film, cm$^{-1}$):
  1720, 1470, 1355, 1260, 1185, 1115, 1075, 905, 840, 785.
NMR (60 MHz, CCl$_4$, ppm):
  0.09 (s, 6H), 0.78 (s, 9H),
  1.96 (dd, J = 3Hz, 19Hz, 1H),
  2.48 (dd, J = 6Hz, 19Hz, 1H),
  4.84 (m, 1H),
  6.94 (dd, J = 1Hz, 7Hz, 1H),
  7.25 (dd, J = 2Hz, 7Hz, 1H).
Mass (m/e, %):
  212 (M$^+$, 6).
UV (methanol solvent, λmax):
  209 mμ.

The product obtained above was thus identified as being 4-t-butyldimethylsiloxycyclopent-2-en-1-one from the foregoing properties.

EXAMPLE 41

(1-A) $\xrightarrow{\text{Step 1-A}}$ (2-A)

Five grams of crude 4-t-butyldimethylsiloxycyclopent-2-en-1-ol (purity 43%) and 2.72 grams of DDQ were treated in 25 milliliters for 16 hours at 60° C., after which the experiment was operated as in Example 40 to obtain 4.57 grams of a crude product.

When this product was vacuum distilled, 1.88 grams of 4-t-butyldimethylsiloxycyclopent-2-en-1-one of 61–63% purity and boiling at 64°–72° C. (0.1 mmHg) was obtained. When this product was purified by dry column chromatography, 1.17 grams of the intended product of 99% purity and exhibiting the same properties as those of Example 40 was obtained. On the other hand, since 0.42 gram of the purified intended product was obtained from the distillation residue, the yield was 75%.

EXAMPLE 42

(1-A) $\xrightarrow{\text{Step 1-A}}$ (2-A)

One gram of crude 4-t-butyldimethylsiloxycyclopent-2-en-1-ol (purity 40%) and 1.4 grams of active manganese dioxide were stirred for 18 hours at room temperature in 25 milliliters of petroleum ether. After completion of the reaction, the solids portion was filtered off, following which the filtrate was distilled off to obtain 0.91 gram of a crude reaction product. On analysis of this product, it was found to contain 40% of 4-t-butyldimethylsiloxycyclopent-2-en-1-one from its agreement with the reference substance. The yield was calculated to be 92%.

EXAMPLE 43

(1-A) _Step 1-A_ (2-A)

0.50 gram of crude 4-t-butyldimethylsiloxycyclopent-2-en-1-ol (purity 40%) and 0.50 gram of active manganese dioxide were stirred in 25 milliliters of petroleum ether and heated under reflux for 6 hours, after which the reaction mixture was treated as in Example 40 to obtain 0.46 gram of a crude product. It was found by gas chromatography that this crude product contained the intended substance having a purity of 40%. The yield was calculated to be 93%.

EXAMPLE 44

(1-A) _Step 1-A_ (2-A)

530 milligrams of (R)-trans-4-t-butyldimethylsiloxycyclopent-2-en-1-ol ($[\alpha]_D^{20} = +67°$) and 1.94 grams of active manganese dioxide were stirred in 50 milliliters of petroleum ether and heated under reflux for 4 hours, after which the reaction mixture was treated as in Example 42 to obtain 448 milligrams of a crude product. This product was found to be a simple substance as a result of its analyses by gas chromatography (carbowax) 20 M, 20%, 180° C.) and thin-layer chromatography (silica gel, hexane:ethyl acetate = 2:3). Hence, its yield was 85%. The optical rotation of this product was $[\alpha]_D^{20} = +32°$ (c = 0.051, methanol).

EXAMPLE 45

(1-A) _Step 1-A_ (2-A)

599 milligrams of (R)-trans-4-t-butyldimethylsiloxycyclopent-2-en-1-ol ($[\alpha]_D^{20} = +124°$) and 2.0 grams of active manganese dioxide were heated under reflux for 6 hours in a solvent mixture of 25 milliliters of petroleum ether and 2 milliliters of dioxane with stirring. When the reaction product was then aftertreated as in Example 42, 480 milligrams of a crude product was obtained. This product was found to be a simple substance by thin-layer chromatography (silica gel, hexane-ethyl ether = 2:3). Hence, the yield was 81%. The optical rotation of this product was $[\alpha]_D^{20} = +51°$ (c = 0.079, methanol).

EXAMPLE 46

(1-A) _Step 1-A_ (2-A)

148 milligrams of (S)-trans-4-t-butyldimethylsiloxycyclopent-2-en-1-ol ($[\alpha]_D^{20} = -17°$) and 1.3 grams of active manganese dioxide were stirred and heated under reflux for about 12 hours in 30 milliliters of petroleum ether, after which the reaction mixture was treated as in Example 42 to obtain 112 milligrams of a crude product. This product was found to be a simple substance from its thin-layer chromatography (silica gel, hexane-ethyl acetate = 2:3). Hence, the yield was 75%. The optical rotation of this product was $[\alpha]_D^{20} = -6.7°$ (c = 0.32, methanol).

EXAMPLE 47

(1-A) _Step 1-A_ (2-A)

214 milligrams of 4-t-butyldimethylsiloxycyclopent-2-en-1-ol was added to a chromic acid-pyridine complex prepared in 20 milliliters of methylene chloride from 600 milligrams of chromic anhydride and 949 milligrams of pyridine, following which the mixture was stirred for 15 minutes at room temperature. After completion of the reaction, the organic layer was separated and then dissolved in ether followed by thorough washing in water, drying with anhydrous sodium sulfate and thereafter distilling off the solvent to obtain 173 milligrams of a crude product. This product was found to be a simple substance from its thin-layer chromatography (silica gel, hexane-ethyl acetate = 2:3), and it was identified as being 4-t-butyldimethylsiloxycyclopent-2-en-1-one from its spectral data. The yield was 82%.

EXAMPLE 48

(1-A) _Step 1-A_ (2-A)

Six milligrams of (R)-trans-5-tetrahydropyranyloxycyclopent-1-en-3-ol was dissolved in a solvent mixture of 3 milliliters of petroleum ether and 0.5 milliliter of benzene, and the resulting solution was refluxed after the addition of 10 milligrams of active manganese dioxide. Six hours later, the resulting precipitate was separated by filtration and, after distilling off the organic solvent, purified by thin-layer chromatography (cyclohexane-ethyl acetate = 7:3) to obtain 4 milligrams (67%) of (R)-4-tetrahydropyranyloxycyclopent-2-en-1-one.

IR (liquid film, cm$^{-1}$):
 1720, 1655.

NMR (CCl$_4$):
 1.60 (6H), 2.32 (2H), 3.63 (2H), 4.80 (2H), 6.10 (1H), 7.58 (1H).

EXAMPLE 49

(1-A) _Step 1-A_ (2-A)

Six milligrams of (S)-trans-5-tetrahydropyranyloxycyclopent-1-en-3-ol was dissolved in a solvent mixture of 3 milliliters of petroleum ether and 0.5 milliliter of benzene, and the resulting solution was refluxed after the addition of 10 milligrams of active manganese dioxide. Six hours later, the resulting precipitate was separated by filtration and, after distilling off the organic solvent, purified by thin-layer chromatography (cyclohexane-ethyl acetate = 7:3) to obtain 4 milligrams (67%) of (S)-4-tetrahydropyranyloxycyclopent-2-en-1-one. The IR and NMR data were in complete agreement with those of the corresponding (R)-isomer.

EXAMPLE 50

(5) _Step 6-B_ (2-B)

1.1 milliliters of a carbon tetrachloride solution (0.55 M) of (+)-alpha-methoxy-alpha-trifluoromethylphenylacetyl chloride (MTPA-Cl) was added to 55 milligrams of 4-hydroxycyclopent-2-en-1-one, to which was then added 5 drops of pyridine, after which the reaction was carried out for about 12 hours at room temperature with stirring. After completion of the reaction, water and ether were added to the reaction product, and the organic layer was separated. This was then washed successively in a 5% aqueous sodium bicarbonate solution, 5% aqueous hydrochloric acid solution, saturated aqueous Glauber's salt solution and water and thereafter dried with anhydrous magnesium sulfate, after which the drying agent was filtered off. When the resulting solution was vacuum distilled, 150 milligrams of a crude product was obtained. When this product was analyzed by thin-layer chromatography (silica gel, hexane:ethyl acetate = 4:6), it exhibited a single spot (Rf = 0.52). The yield was 86%. The properties of this product were as follows:

IR (liquid film, cm$^{-1}$):

1725, 1250, 1170, 1015.
UV (methanol, λmax): 210.
NMR (CDCl$_3$, ppm, 100 MHz):
  2.32, 2.40 (dd, J = 2.5Hz, 19Hz, 1H),
  2.85, 2.93 (dd, J = 6Hz, 19Hz, 1H),
  3.55 (s, 3H), 6.1 (m, 1H),
  6.40, 6.42 (dd, J = 1.5Hz, 6Hz, 1H), 7.44 (m, 5H),
  7.50, 7.56 (dd, J = 2.5Hz, 6Hz, 1H).
Mass (m/e, %):
  314 (M$^+$, 0.1).

EXAMPLE 51

(5) Step 6-B (2-B)

To 10 milligrams of 4-hydroxycyclopent-2-en-1-one ($[\alpha]_D^{20}$ = +59°) was added 0.28 milliliter of a carbon tetrachloride solution (0.47 M) of MTPA-Cl and, after the addition of 2 drops of pyridine, the mixture was stirred for 12 hours at room temperature. The reaction product was then submitted to the same aftertreatment as that described in Example 50 to obtain about 40 milligrams (crude yield 100%) of a crude product. When this product was purified by thin-layer chromatography, 7 milligrams (yield 20%) of the intended product was obtained. From its NMR data, it was found that this product was the R-isomer of the product obtained in Example 50.

EXAMPLE 52

(5) Step 6-B (2-B)

Twenty-six milligrams of (R)-4-hydroxycyclopent-2-en-1-one($[\alpha]_D^{20}$ = +59°) was dissolved in 0.8 millilier of carbon tetrachloride and, after adding 39 milligrams of acetyl chloride thereto, 2 drops of pyridine was added. The reaction of the mixture was then carried out for 48 hours at room temperature with stirring. The reaction product was then aftertreated as in Example 50 to obtain about 27 milligrams of a crude product. This product was found to be a simple substance as a result of its analysis by thin-layer chromatography (silica gel, hexane-ethyl acetate = 4:6). The yield was 73%. The properties of this product were as follows: $[\alpha]_D^{20}$ = +66° (c = 0.017, methanol).
IR (liquid film, cm$^{-1}$):
  1735, 1710.
NMR (60 MHz, CCl$_4$, ppm):
  2.00 (s, 3H), 2.25 (dd, J = 3Hz, 19Hz, 1H), 2.75 (dd, J = 6Hz, 19Hz, 1H), 4.77 (m, 1H), 6.26 (dd, J = 1Hz, 7Hz, 1H), 7.52 (dd, J = 2Hz, 7Hz, 1H).
Mass (m/e, %):
  140 (M$^+$, 3).
UV (methanol solvent, λmax):
  210 nm.

EXAMPLE 53

(5) Step 6-B (2-B)

Nine milligrams of (R)-4-hydroxycyclopent-2-en-1-one ($[\alpha]_D^{20}$ = +59°) was dissolved in 0.5 milliliter of dioxane and, after adding 0.25 milliliter of a carbon tetrachloride solution (0.53 M) of benzoyl chloride and 2 drops of pyridine, the reaction was carried out by allowing the mixture to stand for 12 hours at room temperature. The reaction product was then aftertreated as in Example 50 to obtain 9 milligrams (yield 45%) of a crude product. When the so obtained product was purified by thin-layer chromatography, 4 milligrams (yield 22%) of (R)-4-hydroxycyclopent-2-en-1-one was obtained. The properties of this product were as follows:
IR (liquid film, cm$^{-1}$):
  3050, 1730, 1715, 1270, 1110, 795, 710.
UV (methanol solvent, λmax):
  228 nm.
NMR (CDCl$_3$, ppm, 100 Hz):
  2.52 (dd, J = 2Hz, 19Hz, 1H), 2.96 (dd, J = 6Hz, 19Hz, 1H), 6.12 (m, 1H), 6.44 (dd, J = 1.5Hz, 6Hz, 1H), 7.72 (dd, J = 2.5Hz, 6Hz, 1H), 7.53 (m, 3H), 8.06 (dd, J = 2Hz, 8Hz, 2H).
Mass (70 eV, m/e, %):
  202 (M$^+$, 14).
CD (methanol, λmax):
  Δε227 = +31°.

EXAMPLE 54

(5) Step 6-A (2-A)

Twenty-five milligrams of crude (R)-4-hydroxycyclopent-2-en-1-one ($[\alpha]_D^{20}$ = +49°) and 35 milligrams of imidazole were dissolved in 0.4 milliliter of dimethylformamide. To the resulting solution was added 38 milligrams of t-butyldimethylsilyl chloride, after which the reaction was carried out by allowing the mixture to stand at room temperature for 15 hours. After completion of the reaction, water and hexane were added to the reaction product, following which the organic layer was separated. The separated organic layer was wahsed in water and dried with sulfuric anhydride, after which the drying agent was separated by filtration, and the solvent was distilled off to obtain 56 milligarms (crude yield 100%) of a crude product. This product was purified by thin-layer chromatography to obtain 8 milligrams (yield 16%) of (R)-4-t-butyldimethylsiloxycyclopent-2-en-1-one. The properties of this product were as follows: $[\alpha]_D^{20}$ = +53° (c = 0.11, methanol).
CD (methanol, λmax):
  Δε218 = +19°.
IR (liquid film, cm$^{-1}$):
  1720.
NMR (60 MHz, CCl$_4$, ppm):
  0.09 (s, 6H), 0.87 (s, 9H), 2.04 (dd, J = 3Hz, 19Hz, 1H), 2.57 (dd, J = 6Hz, 19Hz, 1H), 4.93 (m, 1H), 7.03 (dd, J = 1Hz, 7Hz, 1H), 7.34 (dd, J = 2Hz, 7Hz, 1H).
Mass (m/e, %):
  212 (M$^+$, 5).
UV (methanol solvent, λmax):
  209 nm

EXAMPLE 55

(6-A) Step 7 (5)

Thirty milligrams of the (R)-t-butyldimethylsiloxycyclopent-2-en-1-one ($[\alpha]_D^{20}$ = +32°) obtained in Example 44 was placed in an acetic acid-water-tetrahydrofuran (3:1:1) solvent mixture and reacted by allowing the mixture to stand at room temperature for 48 hours. Toluene was then added to the reaction product, and the acetic acid, water and tetrahydrofuran were azeotropically distilled off under reduced pressure to obtain 13 milligrams (yield 94%) of a crude product. When this product was analyzed by thin-layer chromatography (hexane-ethyl acetate = 4:6), it exhibited a single spot at Rf = 0.15. The specific rotatory power of this product was $[\alpha]_D^{20}$ = +36°. The properties of this product were as follows:
IR (liquid film, cm$^{-1}$).

3430, 1710, 1660, 1255, 1105, 11045.
UV (methanol, λmax):
  209 nm.
NMR (60 MHz, CDCl$_3$, δ(ppm)):
  2.33 (dd, J = 3Hz, 19Hz, 1H), 2.84 (dd, J = 7Hz, 19Hz, 1H), 3.58 (s, 1H), 5.13 (bs, 1H), 6.23 (d, J = 6Hz, 1H), 7.63 (dd, J = 2Hz, 6Hz, 1H).
Mass (70 eV, m/e, %): 98 (M$^+$, 100).

The product was thus identified as being (R)-4-hydroxycyclopent-2-en-1-one from the foregoing data.

EXAMPLE 56

(2-A) $\xrightarrow{Step\ 7}$ (5)

The (S)-4-t-butyldimethylsiloxycyclopent-2-en-1-one ([α]$_D^{20}$ = −6.7°) obtained in Example 46 was added to 3 milliliters of an acetic acid-water-tetrahydrofuran (3:1:1) solvent mixture, and the mixture was reacted by allowing it to stand at room temperature for 43 hours. After completion of the reaction, toluene was added to the reaction solution, and all of the solvnets were azeotropically distilled off to obtain 8 milligrams (yield 80%) of the intended product. The specific rotatory power of this product was [α]$_D^{20}$ = −5°. From the fact that the spectral data of IR, UV, NMR and Mass were in agreement with those of 4-hydroxycyclopent-2-en-1-one, this product was confirmed to be (S)-4-hydroxycyclopent-2-en-1-one.

EXAMPLE 57

(1-B) $\xrightarrow{Step\ 8}$ (3)

After dissolving 28 milligrams of (R)-trans-5-hydroxycyclopent-1-one ([α]$_D^{20}$ = +258°) in 1.0 milliliter of ether, this solution was added at 0° C. to a solution of 10 milligrams of lithium aluminum hydride in 3 milliliters of ether, following which the mixture was held for 10 minutes at room temperature. Several drops of a saturated aqueous solution of sodium sulfate was then added to the reaction product, after which the white precipitate separating out was separated and removed, washed in ether, and the ether was distilled off from the organic layer to obtain 12 milligrams (yield 60%) of the intended product ([α]$_D^{20}$ = +200° (c - 0.004, methanol)). The spectral data of IR, Mass and NMR of this product were in agreement with those of a separately prepared trans-3,5-dihydroxycyclopent-1-ene. Thus, from this fact it was confirmed to be (R)-trans-3,5-dihydroxycyclopent-1-ene.

We claim:

1. An (R)- or (S)-4-hydroxy (or protected hydroxy)-cyclopent-2-en-1-one compound represented by the following formula

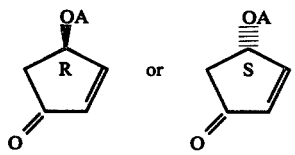

wherein
  A is selected from the group consisting of a hydrogen atom, t-butyldimethylsilyl group, tetrahydropyranyl group and acetyl group.

2. (S)-4-(t-butyldimethylsiloxy)cyclopent-2-en-1-one of the formula

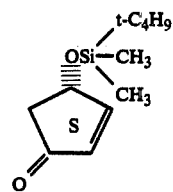

3. (R)-4-(tetrahydropyranyloxy)cyclopent-2-en-1-one of the formula

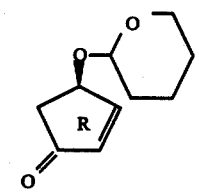

4. (S)-4-(tetrahydropyranyloxy)cyclopent-2-en-1-one of the formula

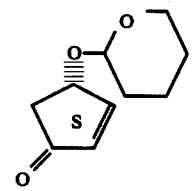

5. (R)-4-acetoxycyclopent-2-en-1-one of the formula

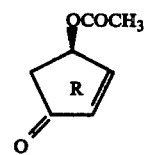

6. (S)-4-acetoxycyclopent-2-en-1-one of the formula

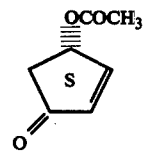

7. (R)-4-benzoyloxycyclopent-2-en-1-one of the formula

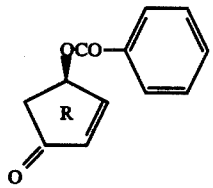

8. (S)-4-benzoyloxycyclopent-2-en-1-one of the formula 9. (R)-4-[(+)-alpha-methoxy-alpha-trifluoromethyl-phenylacetoxy]cyclopent-2-en-1-one of the formula
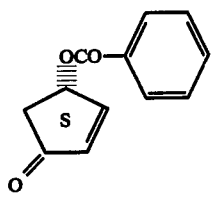
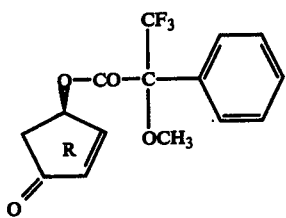
10. (S)-4-[(+)-alpha-methoxy-alpha-trifluoromethyl-phenylacetoxy]cyclopent-2-en-1-one of the formula
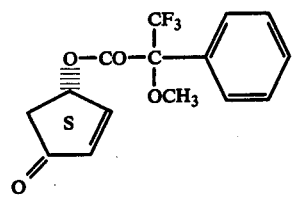
11. (R)-4-(t-butyldimethylsiloxy)cyclopent-2-en-1-one of the formula
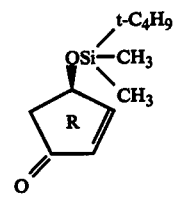
12. (R)-4-hydroxycyclopent-2-en-1-one of the formula
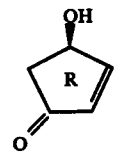
13. (S)-4-hydroxycyclopent-2-en-1-one of the formula
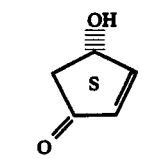
* * * * *